United States Patent
Chaturvedi et al.

(10) Patent No.: US 7,081,465 B2
(45) Date of Patent: Jul. 25, 2006

(54) ALPHA-SUBSTITUTED NAPHTHYLOXY OMEGA-SUBSTITUTED ALKY/ARYL AMINO-SUBSTITUTED ALKANE DERIVATIVES AS AGENT FOR TREATMENT OR PROPHYLAXIS OF DIABETES AND RELATED METABOLIC DISORDERS

(75) Inventors: Devdutt Chaturvedi, Lucknow (IN); Atul Kumar, Lucknow (IN); Reema Rastogi, Lucknow (IN); Arivend Srivastava, Lucknow (IN); Priti Tewari, Lucknow (IN); Rehan Ahmad, Lucknow (IN); Ramaesh Chander, Lucknow (IN); Anju Puri, Lucknow (IN); Geetika Bhatia, Lucknow (IN); Farhar Rivizvi, Lucknow (IN); Anil Kumar Rastogi, Lucknow (IN); Suprabhat Ray, Lucknow (IN)

(73) Assignee: Council of Scientific and Industrial Research, New Delhi (IN)

( * ) Notice: Subject to any disclaimer, the term of this patent is extended or adjusted under 35 U.S.C. 154(b) by 63 days.

(21) Appl. No.: 10/693,098

(22) Filed: Oct. 27, 2003

(65) Prior Publication Data
US 2004/0192688 A1 Sep. 30, 2004

Related U.S. Application Data

(60) Provisional application No. 60/458,413, filed on Mar. 31, 2003.

(51) Int. Cl.
*C07C 217/14* (2006.01)
*C07D 295/088* (2006.01)
*A61K 31/138* (2006.01)
*A61K 31/445* (2006.01)

(52) U.S. Cl. ...................... 514/319; 514/510; 514/651; 546/206; 560/39; 564/352

(58) Field of Classification Search ................ 546/206; 564/352; 514/319, 651, 510; 560/39
See application file for complete search history.

(56) References Cited

U.S. PATENT DOCUMENTS 2,133,779 A * 10/1938 Clifford ....................... 524/246
2,681,932 A * 6/1954 Cusic et al. ................ 564/287
4,260,816 A * 4/1981 Albright et al. ............ 562/452

OTHER PUBLICATIONS

Flanders et al., Autoimmunity, 29(3), 235-246, 1999.*
Rosenbloom et al., Clinical Pediatrics, 37, 2, 143-152, Feb. 1988.*

* cited by examiner

*Primary Examiner*—Fiona T. Powers
(74) *Attorney, Agent, or Firm*—Sughrue Mion, PLLC

(57) ABSTRACT

This invention relates to novel ω-substituted-naphthyloxy-amino alkanes, their preparation and use as antihyperglycemic agents and for the treatment and prevention of cardiovascular disorders (CVS) such as lipid lowering effects.

95 Claims, No Drawings

ALPHA-SUBSTITUTED NAPHTHYLOXY OMEGA-SUBSTITUTED ALKY/ARYL AMINO-SUBSTITUTED ALKANE DERIVATIVES AS AGENT FOR TREATMENT OR PROPHYLAXIS OF DIABETES AND RELATED METABOLIC DISORDERS

This application claims benefit of Provisional Application No. 60/458,413 field Mar. 31, 2003; the disclosure of which is incorporated herein by reference.

FIELD OF INVENTION

This invention relates to novel ωsubstituted-naphthyloxy-amino alkanes, their preparation and use as antihyperglycemic agents and for the treatment and prevention of cardiovascular disorders (CVS) such as lipid lowering effects.

BACKGROUND OF THE INVENTION

An analysis of the molecular structure of active PPARγ-agonists mentioned above would suggest the presence of three distinct substructures. (I) the thiazolidine 2,4-dione unit 'A', (ii) the intermediate alkyl chain 'B' and (iii) the aryl substituent 'C'. Since the thiazolidine 2,4-dione derivatives are associated with side effects such as liver toxicity etc, a molecular modification to eliminate such a unit was considered desirable. In the present invention the thiazolidine 2,4-dione unit has been replaced by substituted amino residues which has resulted in novel compounds showing the desired anti-hyperglycemic activity along with lipid lowering activity which is an added desirable activity.

FIG.-1: Structure of PPARγ-agonists

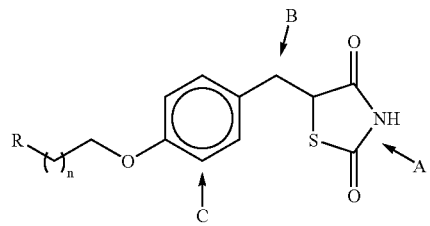

Prior Art

PPARγ-agonists which act as insulin sensitizers are showing promise in the treatment of NIDDM (Type II diabetes) which is a disease prevalent in developed as well as developing countries. A number of agents show PPARγ agonist activity. Most of these compounds are thiazolidine 2,4-dione derivatives. Some of the compounds belonging to this class which have entered in clinic are Pioglitazone (Momose, Y.; Takeda, H.; Hatanaka, C.; Oi, S.; Sohda, T. Chem. Pharm. Bull. 1991, 39, 1440–1445), Rosiglitazone (Cantello, B. C. C.; Cawthome, M. A.; Haigh, D.; Hindley, R. M.; Smith, S. A.; Thurlby, P. L. Bio-org. Med. Chem. Lett. 1994, 4, 1181–1184), Netoglitazone (Viton, R.; Widdowson, P. S.; Ishii, S.; Tanaka, H.; Wikllain, G. British J. Pharmacolgy 1998, 125, 1708–14), Troglitazone(Yoshida, T.; Fujita, T.; Kanai, T.; et al J. Med. Chem. 1989, 32, 421–428).

OBJECT OF THE INVENTION

The object of the present invention relates to novel ω-substituted-naphthyloxy-amino alkanes derivatives having structural formula I.

Another object of the present invention relates to the process of preparing novel ω-substituted-naphthyloxy-amino alkanes derivatives having structural formula I.

Another object of the present invention relates to the process of preparing novel ω-substituted-naphthyloxy-amino alkanes derivatives having structural formula I.

Yet another object of the present invention relates to the to a pharmaceutical composition for the treatment or prevention of cardiovascular disorders (CVS) and of hyperglycemic condition (diabetes) in mammals, including humans, said composition comprising of administering effective dosage of novel ω-naphthyloxy amino alkane derivatives having structural Formula 1 optionally along with acceptable salt/s, carrier/s or dilutent/s. Still another object of the present invention relates to a method for treatment or prevention of cardiovascular disorders and hyperglycemia (diabetes) by administering pharmaceutical effective dosage of ω-naphthyloxy amino alkane derivatives having structural Formula 1,

DESCRIPTION OF THE INVENTION

This invention relates to novel ω-substituted-naphthyloxy-amino alkanes, their preparation and use as antihyperglycemic agents and for the treatment and prevention of cardiovascular disorders(CVS) such as lipid lowering effects. The main objective of the present invention is to provide agents to act in NIDDM with the added advantage of their effect in lowering low density cholesterol(LDL) without affecting high density cholesterol (HDL) in the treatment and prevention of CVS disorders.

Accordingly, the main embodiment of present invention relates to novel ω-naphthyloxy amino alkane derivatives having structural formula I,

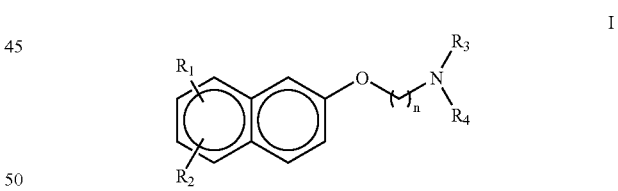

Wherein $R_1$ and $R_2$ are individually H, a lower alkyl containing 1–6 carbon atoms, such as methyl, ethyl, propyl, butyl, pentyl, hexyl; a branched chain lower alkyl such as isopropyl, isobutyl, t-butyl and alkyl chains thereof.; a cyclic alkane such as cyclopropyl, cyclobutyl, cyclohexyl, cycloheptyl and cyclic alkanes thereof.; a lower alkoxy in which the alkyl group is as mentioned above, n is 1 to 6; $R_3$ and $R_4$ are individually H, a lower straight or branched chain alkyl containing 1–15 carbon atoms as mentioned above; a cyclic alkane as defined above; an aryl residue selected from group comprising of phenyl, substituted phenyl, naphthyl; an arylalkyl residue selected from group comprising of benzyl, substituted benzyl, form a part of a heterocyclic ring selected from group comprising of pyrrolidine, piperidine, form a heterocyclic ring with additional heteroatoms O,N,S selected from group comprising of piperazine, morpholine, oxazole, oxathinazole, oxathiazine etc.; an alkoxy carbonyl alkane selected from $R_6COOR_7$, wherein $R_6$ is $(CH_2)_n$ (n=1–3) and $R_7$ is a lower alkyl as defined above.

Another embodiment of the present invention relates to preferred novel ω-naphthyloxy amino alkane derivatives comprising of (i) N-(4-Methoxyphenyl)-[3-(naphthalen-2-yloxy)propyl]amine[I: $R_1=R_2=R_3=H$, $R_4$=4-methoxyphenyl, n=3]

(ii) N-(4-Methoxyphenyl)-N-propyl[3-(naphthalen-2-yloxy)propylamine[I: $R_1=R_2=H$, $R_3$=propyl $R_4$=4-methoxyphenyl, n=3]

(iii) N-(4-Methoxyphenyl)-[3-(naphthalen-2-yloxy)propyl]amino}acetic acid ethyl ester.[I: $R_1=R_2=H$, $R_3=CH_2COOEt$, $R_4$=4-methoxyphenyl, n=3]

(iv) N-Benzyl-[2-(naphthalen-2-yloxy)-ethyl]amine[I: $R_1=R_2=R_3=H$, $R_4$=benzyl, n=2]

(v) N-(4-Methoxyphenyl)-[2-(naphthalen-2-yloxy)ethyl]amine[I: $R_1=R_2=R_3=H$, $R_4$=4-methoxyphenyl, n=2]

(vi) N-(4-Methoxyphenyl)-[3-(naphthalen-2-yloxy)propyl]amine[I: $R_1=R_2=R_3=H$, $R_4$=4-methoxyphenyl, n=3]

(vii) N-(4-Methoxyphenyl)-[4-(naphthalen-2-yloxy)butylamine[I: $R_1=R_2=R_3=H$, $R_4$=4-methoxyphenyl, n=4]

(viii) N-(4-Methylphenyl)-[2-(naphthalen-2-yloxy)ethyl]amine[I: $R_1=R_2=R_3=H$, $R_4$=4-methylphenyl, n=2]

(ix) N-(4-Methylphenyl)-[3-(naphthalen-2-yloxy)propyl]amine[I: $R_1=R_2=R_3=H$, $R_4$=4-methylphenyl, n=3]

(x) N-(4-Methylphenyl)-[4-(naphthalen-2-yloxy)butyl]amine[I: $R_1=R_2=R_3=H$, $R_4$=4-methylphenyl, n=4]

(xi) N-(3-Methoxybenzyl)-[2-napthalen-2-yloxy)ethyl]amine[I: $R_1=R_2=R_3=H$, $R_4$=3-methoxybenzyl, n=2]

(xii) N-(3-Methoxybenzyl)-[3-napthalen-2-yloxy)propyl]amine[I: $R_1=R_2=R_3=H$, $R_4$=3-methoxybenzyl, n=3]

(xiii) N-(3-Methoxybenzyl)-[4-napthalen-2-yloxy)butyl]amine[I: $R_1=R_2=R_3=H$, $R_4$=3-methoxybenzyl, n=4]

(xiv) N-Benzyl-[2-(naphthalen-2-yloxy)-ethyl]amine[I: $R_1=R_2=R_3=H$, $R_4$=benzyl, n=2]

(xv) N-Benzyl-[3-(naphthalen-2-yloxy)-propyl]amine[I: $R_1=R_2=R_3=H$, $R_4$=benzyl, n=3]

(xvi) N-Benzyl-[4-(naphthalen-2-yloxy)-butyl]amine[I: $R_1=R_2=R_3=H$, $R_4$=benzyl, n=4]

(xvii) N-Cyclohexyl-[2-(naphthalen-2-yloxy)-ethyl]amine[I: $R_1=R_2=R_3=H$, $R_4$=cylohexyl, n=2]

(xviii) N-Cyclohexyl-[3-(naphthalen-2-yloxy) propyl]amine [I: $R_1=R_2=R_3=H$, $R_4$=cylohexyl, n=3]

(xix) N-Cyclohexyl-[4-(naphthalen-2-yloxy)-butyl]amine [I: $R_1=R_2=R_3=H$, $R_4$=cylohexyl, n=4]

(xx) N-(2-Ethyl-n-hexyl)-[2-(naphthalen-2-yloxy)ethyl]amine[I: $R_1=R_2=R_3=H$, $R_4$=2-ethyl n-hexyl, n=2]

(xxi) N-(2-Ethyl-n-hexyl)-[3-(naphthalen-2-yloxy)propyl]amine[I: $R_1=R_2=R_3=H$, $R_4$=2-ethyl-n-hexyl, n=3].

(xxii) N-(2-Ethyl-n-hexyl)-[4-(naphthalen-2-yloxy)butyl]amine[I: $R_1=R_2=R_3=H$, $R_4$=2-ethyl-n-hexyl, n=4]

(xxiii) N-(n-Dodecyl)-[2-(naphthalen-2-yloxy)-ethyl]amine[I: $R_1=R_2=R_3=H$, $R_4$=n-dodecyl, n=2]

(xxiv) N-(n-Dodecyl)-[3-(naphthalen-2-yloxy)-propyl]amine[I: $R_1=R_2=R_3=H$, $R_4$=n-dodecyl, n=3]

(xxv) N-(n-Dodecyl)-[4-(naphthalen-2-yloxy)-butyl]amine[I: $R_1=R_2=R_3=H$, $R_4$=n-dodecyl, n=4]

(xxvi) N-(Isoamyl)-[2-(naphthalen-2-yloxy)ethyl]amine [I: $R_1=R_2=R_3=H$, $R_4$=isoamyl, n=2]

(xxvii) N-(Isoamyl)-[3-(naphthalen-2-yloxy)propyl]amine[I: $R_1=R_2=R_3=H$ $R_4$=isoamyl, n=3]

(xxviii) N-(Isoamyl)-[4-(naphthalen-2-yloxy)-butyl]amine[I: $R_1=R_2=R_3=H$, $R_4$=isoamyl, n=4]

(xxix) N-(3-Phenylpropyl)-[2-(naphthalen-2-yloxy)ethyl]amine[I: $R_1=R_2=R_3=H$, $R_4$=2-phenylethyl, n=2]

(xxx) N-(3-Phenylpropyl)-[3-(naphthalen-2-yloxy)propyl]amine[I: $R_1=R_2=R_3=H$, $R_4$=2-phenylethyl, n=3]

(xxxi) N-(3-Phenylpropyl)-[4-(naphthalen-2-yloxy)butyl]amine[I: $R_1=R_2=R_3=H$, $R_4$=2-phenylethyl, n=4]

(xxxii) N-(n-Octyl)-[2-(naphthalen-2-yloxy)ethyl]amine [I: $R_1=R_2=R_3=H$, $R_4$=n-octyl, n=2]

(xxxiii) N-(n-Octyl)-[3-(naphthalen-2-yloxy)propyl]amine[I: $R_1=R_2=R_3=H$, $R_4$=n-octyl, n=3]

(xxxiv) N-(n-Octyl)-[3-(napthalen-2-yloxy)butyl]amine [I: $R_1=R_2=R_3=H$, $R_4$=n-octyl, n=4]

(xxxv) N-(n-Butyl)-[4-(naphthalen-2-yloxy)butyl]amine [I: $R_1=R_2=R_3=H$, $R_4$=n-butyl, n=4]

(xxxvi) N-(n-Propyl)-[4-(naphthalen-2-yloxy)butyl]amine[I: $R_1=R_2=R_3=H$, $R_4$=n-propyl, n=4]

(xxxvii) N-(2-Phenylethyl)-[2-(naphthalen-2-yloxy)butyl]amine[I, $R_1=R_2=R_3=H$, $R_4$=2-phenyl-ethyl, n=4]

(xxxviii) N-(Piperidinyl)-[4-(naphthalen-2-yloxy)butyl]amine[I, $R_1=R_2=R_3=H$, $R_4$=Piperidinyl, n=4]

(xxxix) N-(n-Butyl)-[3-(naphthalen-2-yloxy)propyl]amine[I, $R_1=R_2=R_3=H$, $R_4$n-butyl, n=3]

(xl) N-(n-Propyl)-[3-(naphthalen-2-yloxy) propyl]amine [I, $R_1=R_2=R_3=H$, $R_4$=n-propyl, n=3]

(xli) N-(2-Phenylethyl)-[3-(naphthalen-2-yloxy)propyl]amine[I, $R_1=R_2=R_3=H$, $R_4$=2-phenylethyl, n=3]

(xlii) N-(Piperidinyl)-[3-(naphthalen-2-yloxy)propyl]amine[I, $R_1=R_2=R_3=H$, $R_4$=Piperidinyl, n=3]

(xliii) N-(4-Methoxyphenyl)-N-methyl[3-(naphthalen-2-yloxy)propylamine,[I, $R_1=R_2=H$, $R_3$=methyl, $R_4$=4-methoxyphenyl, n=3]

(xliv) N-(4 Methoxyphenyl)-N-ethyl[3-(naphthalen-2-yloxy)propylamine.[I, $R_1=R_2=H$, $R_3$=ethyl, $R_4$=4-methoxyphenyl, n=3]

(xlv) N-(4-Methoxyphenyl)-N-propyl[3-(naphthalen-2-yloxy)propylamine[I, $R_1=R_2=H$, $R_3$=propyl, $R_4$=4-methoxyphenyl, n=3]

(xlvi) N-(4-Methoxyphenyl)-N-butyl[3-(naphthalen-2-yloxy)propylamine[I, $R_1=R_2=H$, $R_3$=n-butyl, $R_4$=4-Methoxyphenyl, n=3]

(xlvii) N-(4-Methoxyphenyl)-[3-(naphthalen-2-yloxy) propyl]amino}acetic acid ethyl ester[I, $R_1=R_2=H$, $R_3$=—$CH_2COOEt$, $R_4$=4-Methoxyphenyl, n=3]

(xlviii) 2,7-Bis[3-(4 methoxyphenylamino)propyloxy] naphthalene[I, $R_1$=4-methoxyphenyl amino propyloxy, $R_2$ & $R_3$=H, $R_4$=4-methoxyphenyl]

(xlix) 2,6-Bis[3-(4-methoxyphenylamino)propyloxy] naphthalene[I, $R_2$=4-methoxyphenyl amino propyloxy, $R_1$ & $R_3$=H, $R_4$=4-methoxyphenyl]

Another embodiment of the present invention relates to a method for preparing ω-naphthyloxy amino alkane derivatives having structural formula I,

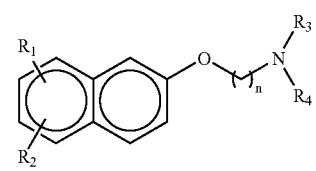

I

Wherein $R_1$ and $R_2$ are individually H, a lower alkyl containing 1–6 carbon atoms, such as methyl, ethyl, propyl, butyl, pentyl, hexyl; a branched chain lower alkyl such as isopropyl, isobutyl, t-butyl etc.; a cyclic alkane such as cyclopropyl, cyclobutyl, cyclohexyl, cycloheptyl etc.; a lower alkoxy in which the alkyl group is as mentioned above, n is 1 to 6; $R_3$ and $R_4$ are individually H, a lower straight or branched chain alkyl containing 1–15 carbon atoms as mentioned above; a cyclic alkane as defined above; an aryl residue such as phenyl, substituted phenyl, naphthyl; an arylalkyl residue such as benzyl, substituted benzyl, form a part of a heterocylic ring such as pyrrolidine, piperidine, form a heterocylic ring with additional heteroatoms O,N,S such as piperazine,morpholine, oxazole, oxathinazole, oxathiazine etc.; an alkoxy carbonyl alkane such as $R_6COOR_7$, wherein $R_6$ is $(CH_2)n$ (n=1–3) and $R_7$ is a lower alkyl as defined above, said process comprising steps of:

(a) reacting substituted β-naphthol of Formula II with dihaloalkane of formula III in an organic solvent in the presence of a base to obtain an intermediate compound of formula IV, and

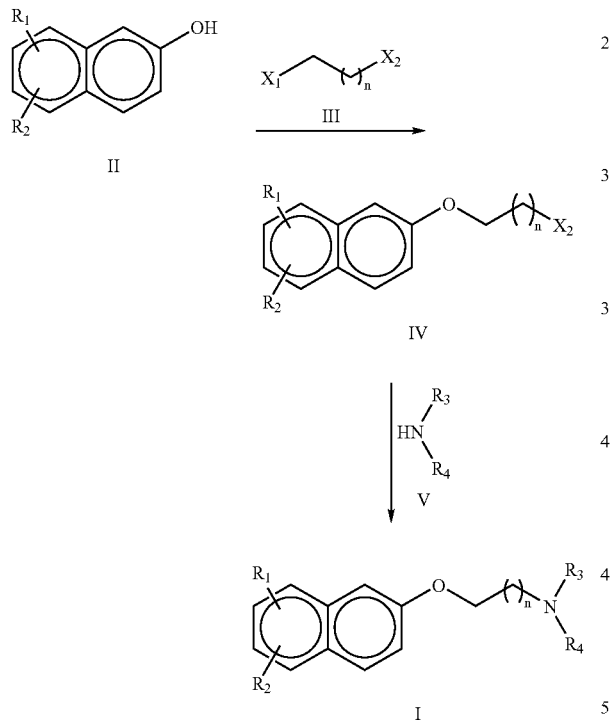

Wherein $R_1$ and $R_2$ are defined as above and wherein $X_1$ and $X_2$ may be same or different halogens, and (b) reacting compound of formula IV with an amine of formula V in presence of an acid binding agent optionally in an organic solvent to obtain compound of formula I, wherein $X_2$ is a halogen and $R_3$ and $R_4$ are defined as above.

Another embodiment of the present invention relates to base in step (a) wherein the said base is selected from a group comprising of cesium carbonate, potassium carbonate, sodium carbonate, lithium carbonate or other bases.

Yet another embodiment of the present invention relates to the organic solvents in step (b) wherein the said organic solvents are selected from group comprising of dimethyl sulphoxide (DMSO), dimethylformamide (DMF), Hexamethylphosphoric triamide (HMPA) or acetonitrile.

Yet another embodiment of the present invention relates to temperature wherein the said temperature in step (a) is in range of about 50° C. to 100° C., Yet another embodiment of the present invention relates to temperature wherein the said temperature is preferably in the range of about 60° C. to 80° C.

Still another embodiment of the present invention relates to temperature wherein the said temperature in step (b) in the range of about 120° C. to 180° C.

Still another embodiment of the present invention relates to temperature wherein the said temperature is preferably in the range of about 130° C. to 150° C.

Still another embodiment of the present invention relates to the reaction time in steps (a) and (b) wherein said reaction time is in range of about 4 hours to 13 hours.

In one more embodiment of the present invention relates to the derivatives of formula (1) wherein the said derivatives have their melting points in the range of about 75° C. to 270° C.

In one more embodiment of the present invention relates to the purity of the derivatives of formula (1) wherein the purity of the said derivatives is in the range of about 80% to 100%.

Another embodiment of the present invention relates to a pharmaceutical composition for the treatment or prevention of cardiovascular disorders (CVS) and of hyperglycemic condition (diabetes) in mammals, including humans, said composition comprising of administering effective dosage of novel ω-naphthyloxy amino alkane derivatives having structural Formula 1,

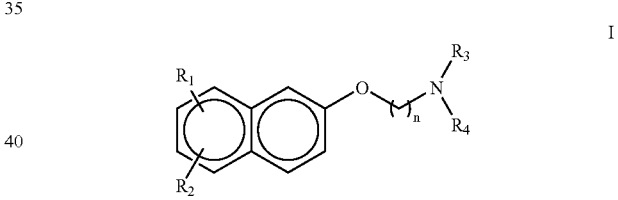

Wherein, $R_1$ and $R_2$ are individually H, a lower alkyl containing 1–6 carbon atoms, such as methyl, ethyl, propyl, butyl, pentyl, hexyl; a branched chain lower alkyl such as isopropyl, isobutyl, t-butyl etc.; a cyclic alkane such as cyclopropyl, cyclobutyl, cyclohexyl, cycloheptyl etc.; a lower alkoxy in which the alkyl group is as mentioned above, n is 1 to 6; $R_3$ and $R_4$ are individually H, a lower straight or branched chain alkyl containing 1–15 carbon atoms as mentioned above; a cyclic alkane as defined above; an aryl residue such as phenyl, substituted phenyl, naphthyl; an arylalkyl residue such as benzyl, substituted benzyl, form a part of a heterocylic ring such as pyrrolidine, piperidine, form a heterocylic ring with additional heteroatoms O,N,S such as piperazine,morpholine, oxazole, oxathinazole, oxathiazine and compounds thereof; an alkoxy carbonyl alkane such as $R_6COOR_7$, wherein $R_6$ is $(CH_2)n$ (n=1–3) and $R_7$ is a lower alkyl as defined above, optionally along with acceptable salt/s, carrier/s or dilutent/s.

Yet another embodiment of the present invention relates to a method for treatment or prevention of cardiovascular disorders and hyperglycemia (diabetes) by administering pharmaceutical effective dosage of ω-naphthyloxy amino alkane derivatives having structural Formula 1,

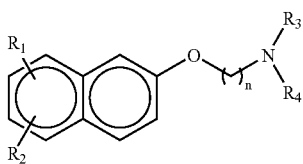

I

Wherein $R_1$ and $R_2$ are individually H, a lower alkyl containing 1–6 carbon atoms, such as methyl, ethyl, propyl, butyl, pentyl, hexyl; a branched chain lower alkyl such as isopropyl, isobutyl, t-butyl etc.; a cyclic alkane such as cyclopropyl, cyclobutyl, cyclohexyl, cycloheptyl etc.; a lower alkoxy in which the alkyl group is as mentioned above, n is 1 to 6; $R_3$ and $R_4$ are individually H, a lower straight or branched chain alkyl containing 1–15 carbon atoms as mentioned above; a cyclic alkane as defined above; an aryl residue such as phenyl, substituted phenyl, naphthyl; an arylalkyl residue such as benzyl, substituted benzyl, form a part of a heterocylic ring such as pyrrolidine, piperidine, form a heterocylic ring with additional heteroatoms O,N,S such as piperazine, morpholine, oxazole, oxathinazole, oxathiazine and compounds thereof; an alkoxy carbonyl alkane such as $R_6COOR_7$, wherein $R_6$ is $(CH_2)n$ (n=1–3) and $R_7$ is a lower alkyl as defined above, optionally along with acceptable salt/s, carrier/s or dilutent/s.

Another embodiment of the present invention relates to the salts/carriers/diluents selected from a group consisting of lactose, sodium chloride, potassium chloride, magnesium sulphate, magnesium chloride, potassium sulfate, sodium sulfate, lithium sulphate, sodium phosphate, potassium phosphate, magnesium succinate, sodium carbonate, sodium sulfate, potassium acid phosphate or calcium bicarbonate.

Another embodiment of the present relates to derivatives wherein the said derivatives may be administered in form syrup, capsule, tablet, intravenous, liquid or suspension.

One more embodiment of the present invention relates to derivatives wherein method of administration for said derivatives may be oral, nasal, rectoral, or parenteral.

One more embodiment of the present invention relates to derivatives wherein said derivatives lower the concentration of cholesterol by about 30%.

One more embodiment of the present invention relates to derivatives wherein said derivatives lower the concentration of cholesterol preferably by about 26%.

Another embodiment of the present invention relates to derivatives wherein the said derivatives lower the concentration of phospholipid by about 35%.

Another embodiment of the present invention relates to derivatives wherein the said derivatives lower the concentration of phospholipid preferably by about 30%.

Another embodiment of the present invention relates to derivatives wherein the said derivatives lower the concentration of Triglyceride by about 50%

Yet another embodiment of the present invention relates to derivatives wherein the said derivatives lower the concentration of Triglyceride preferably by about 48%.

Yet another embodiment of the present invention relates to derivatives wherein the dosage of the said derivatives is in the range of about 250–350 μmol/Kg., Yet another embodiment of the present invention relates to derivatives wherein the dosage of the said derivatives is preferably about 300 μmol/Kg.

One more embodiment of the present invention relates to derivatives wherein said derivatives enhances the high-density lipoprotein (HDL) concentration by about 20%.

Yet another embodiment of the present invention relates to derivatives wherein said derivatives enhances the high-density lipoprotein concentration preferably by about 14%.

Still another embodiment of the present invention relates to derivatives where said derivatives lowers the glucose (GLU) concentration to about 35%.

Still another embodiment of the present invention relates to derivatives wherein said derivatives lowers the glucose concentration preferably to about 30%.

Another embodiment of the present invention relates to derivatives wherein said derivatives lowers the glycerol (GLY) concentration by about 18%.

Yet another embodiment of the present invention relates to derivatives wherein the said derivatives lowers the glycerol concentration by about 14%.

Yet another embodiment of the present invention relates to derivatives wherein the said derivatives lower the glucose concentration in about 30 min to 10 hours during post drug administration.

Still another embodiment of the present invention relates to derivatives wherein the said derivatives lower the glucose concentration in about 1 hr to 7 hrs during post drug administration.

EXAMPLES

Example 1

2-(2-Naphthyloxy)-1-chloroethane (IV: $R_1$=$R_2$=H, $X_2$=Cl, n=2)

A mixture of β-naphthol (1 gm, 0.006 mole), anhydrous $K_2CO_3$ (10 gm, in excess) and 1-bromo-2-chloroethane (0.6 ml, 0.006 mole) was refluxed in dry acetone (50 ml) for 6 hours. Reaction mixture was filtered and filtrate was concentrated to get oily compound, which was crystallized with benzene-hexane to give the colorless crystals of pure desired compound. m.p. 94° C., (yield 1.36 gm, 96%).

Example 2

3-(2-Naphthyloxy)-1-chloropropane (IV: $R_1$=$R_2$=H, $X_2$=Cl, n=3)

A mixture of β-naphthol (1 gm, 0.006 mole), anhydrous $K_2CO_3$ (10 gm, in excess) and 1-bromo-3-chloropropane (0.7 ml, 0.006 mole) was refluxed in dry acetone (50 ml) for 6 hours. Reaction mixture was filtered and filtrate was concentrated to get oily compound which was crystallized with benzene-hexane to give the colorless crystals of pure desired compound, m.p. 98° C., (yield 1.5 gm, 97%).

Example 3

4-(2-Naphthyloxy)-1-chlorobutane (IV: $R_1$=$R_2$=H, $X_2$=Cl, n=4)

A mixture of β-naphthol (1gm, 0.006 mole), anhydrous $K_2CO_3$ (10 gm, in excess) and 1-bromo 4-chlorobutane (0.8 ml, 0.006 mole) was refluxed in dry acetone (50 ml) for 6 hours. Reaction mixture was filtered and filtrate was concentrated to get oily compound, which was crystallized with benzene-hexane to give the colorless crystals of pure desired compound, m.p. 112° C., (yield 1.6 gm, 98%).

The method of preparation of compounds of formula I are given in these following examples.

Example 4

N-(4-Methoxyphenyl)-[3-(naphthalen-2-yloxy)propyl]amine [I: $R_1=R_2=R_3=H$,

Method a:

A mixture of anhydrous potassium carbonate (10 gm, in excess) and p-anisidine (0.42 gm, 0.003 mole) was taken in dry DMSO (40 ml). Now 3-(2-naphthyloxy)-1-chloropropane (0.5 gm, 0.002 mole) was added in it. Reaction mixture was refluxed at 140° C. for 7 hrs and the reaction was completed as checked by TLC. Reaction mixture was poured in distilled water (60 ml) and extracted with ethyl acetate thrice. The organic layer was separated and concentrated to get oily compound which was later crystallized by benzene hexane to get N-(4-methoxyphenyl)-[3-(naphthalen-2-yloxy)propyl]amine as yellow solid, m.p. 110° C., (yield 0.66 gm, 95.6%).

Example 4

N-(4-Methoxyphenyl)-[3-(naphthalen-2-yloxy)propyl]amine [I: $R_1=R_2=R_3=H$, $R_4$=4-methoxy phenyl, n=3]

Method b:

A mixture of anhydrous potassium carbonate (10 gm, in excess) and p-anisidine (0.42 gm, 0.003 mole) was taken in dry DMF (40 ml). Now 3-(2-naphthyloxy)-1-chloropropane (0.5 gm, 0.002 mole) was added in it. Reaction mixture was refluxed at 140° C. for 7 hrs and the reaction was completed as checked by TLC. Reaction mixture was poured in distilled water (60 ml) and extracted with ethyl acetate thrice. The organic layer was separated and concentrated to get oily compound which was later crystallized by benzene hexane to get N-(4-methoxyphenyl)-[3-(naphthalen-2-yloxy) propyl]amine as yellow solid, m.p. 110° C., (yield 0.64 gm, 92.5%).

Example 5

N-(4-Methoxyphenyl)-N-propyl-3-(naphthalen-2-yloxy)propylamine. [I:$R_1=R_2$, $R_3$=propyl $R_4$=4-methoxy phenyl, n=3]

A mixture of N-(4-methoxyphenyl)-[3-(naphthalen-2-yloxy)propyl]amine (0.5 gm, 0.002 mole) and propyl bromide (0.54ml, 0.003 mole) was taken in dry acetone (40 ml). It was refluxed for 12 hrs and the progress of reaction checked by TLC. Reaction mixture was filtered and the filtrate was concentrated to get oily compound which was further crystallized by benzene hexane mixture to get N-(4-methoxyphenyl)-N-propyl[3-(naphthalen-2-yloxy)propylamine, yellow solid, m.p. 127° C., (yield 0.67 gm, 95.7%).

Example 6

N-(4-Methoxyphenyl)-[3-(naphthalen-2-yloxy)propyl]amino}acetic acid ethyl ester.[I: $R_1=R_2=H$, $R_3=CH_2COOEt$, $R_4$=4-methoxy phenyl, n=3]

A mixture of N-(4-methoxyphenyl)-[3-(naphthalen-2-yloxy)propyl]amine (0.5 gm, 0.002 mole) and ethyl bromoacetate (0.62 ml, 0.003 mole) was taken in dry acetone (40 ml). It was refluxed for 10 hrs and the progress of reaction checked by TLC. Reaction mixture was filtered and the filtrate was concentrated to get N-(4-methoxyphenyl)-[3-(naphthalen-2-yloxy)propyl] amino} acetic acid ethyl ester, yellow oil, (yield 0.75 ml, 96%).

Example 7

N-Benzyl-[2-(naphthalen-2-yloxy)-ethyl]amine[I: $R_1=R_2=R_3=H$, $R_4$=Benzyl, n=2]

A mixture of anhydrous potassium carbonate (10 gm, in excess) and benzyl amine (0.38 ml, 0.003 mole) was taken in dry DMSO (40 ml). Now 2-(2-naphthyloxy)-1-chloroethane (0.5 gm, 0.002 mole) was added in it. Reaction mixture was refluxed at 140° C. for 7 hrs and the reaction was completed as checked by TLC. Reaction mixture was poured in distilled water (60 ml) and extracted with ethyl acetate thrice. The organic layer was separated and concentrated to get oily compound which was later crystallized by benzene hexane to get N-benzyl-[2-(naphthalen-2-yloxy)-ethyl]amine solid, m.p. 94° C., (yield 0.61 gm, 90.3%).

Example 8

N-(4-Methoxyphenyl)-[2-(naphthalen-2-yloxy)ethyl]amine[I: $R_1=R_2=R_3=H$, $R_4$=4-methoxyphenyl, n=2]

A mixture of anhydrous potassium carbonate (10 gm, in excess) and p-anisidine (0.45 gm, 0.003 mole) was taken in dry dimethylsulphoxide (DMSO, 40 ml). Now 2-(2-naphthyloxy)-1-chloroethane (0.5 gm, 0.002 mole) was added in it. Reaction mixture was refluxed at 145° C. for 7 hrs. The reaction was completed as checked by TLC. Reaction mixture was poured in distilled water (60 ml) and extracted with ethyl acetate thrice. The organic layer was separated and concentrated to get oily compound which was later crystallized by benzene hexane to get N-(4-methoxyphenyl)-[2-(naphthalen-2-yloxy) ethyl] amine yellow solid, m.p. 92° C., (yield 0.67 gm, 94%).

Example 9

N-(4-Methoxyphenyl)-[3-(naphthalen-2-yloxy)propyl]amine[I: $R_1=R_2=R_3=H$, $R_4$=4-methoxyphenyl, n=3]

A mixture of anhydrous potassium carbonate (10 gm, in excess) and p-anisidine (0.42 gm, 0.003 mole) was taken in dry DMSO (40 ml). Now 3-(2-naphthyloxy)-1-chloropropane (0.5 gm, 0.002 mole) was added in it. Reaction mixture was refluxed at 135° C. for 7 hrs and the reaction was completed as checked by TLC. Reaction mixture was poured in distilled water (60 ml) and extracted with ethyl acetate thrice. The organic layer was separated and concentrated to get oily compound which was later crystallized by benzene hexane to get N-(4-methoxyphenyl)-[3-(naphthalen-2-yloxy)propyl]amine yellow solid, m.p. 110° C., (yield 0.66 gm, 95.6%).

Example 10

N-(4-Methoxyphenyl)-[4-(naphthalen-2-yloxy)buty-lamine [I: $R_1=R_2=R_3=H$, $R_4$=4-methoxyphenyl, n=4]

A mixture of anhydrous potassium carbonate (10 gm, in excess) and p-anisidine (0.4 gm, 0.003 mole) was taken in dry DMSO (40 ml). Now 4-(2-naphthyloxy)-1-chlorobutane (0.5 gm, 0.002 mole) was added in it. Reaction mixture was refluxed at 130° C. for 7 hrs. and the reaction was completed as checked by TLC. Reaction mixture was poured in distilled water (60 ml) and extracted with ethyl acetate thrice. The organic layer was separated and concentrated to get as oily compound which was later crystallized by benzene hexane to get N-(4-methoxyphenyl)-[4-(naphthalen-2-yloxy)butyl]amine, yellow solid, m.p 95° C., (yield 0.67 gm, 97.8%).

Example 11

N-(4-Methylphenyl)-[2-(naphthalen-2-yloxy)ethyl] amine [I: $R_1=R_2=R_3=H$, $R_4$=4-methylphenyl, n=2]

A mixture of anhydrous potassium carbonate (10 gm, in excess) and p-toluedine (0.39 gm, 0.003 mole) was taken in dry DMSO (40 ml). Now 2-(2-naphthyloxy)-1-chloroethane (0.5 gm, 0.002 mole) was added in. Reaction mixture was refluxed at 140° C. for 8 hrs and the reaction was completed as checked by TLC. Reaction mixture was poured in distilled water (60 ml) and extracted with ethyl acetate thrice. The organic layer was separated and concentrated to get oily compound which was later crystallized by benzene hexane to get N-(4-methylphenyl)-[2-(naphthalen-2-yloxy) ethyl] amine, yellow solid, m.p 92° C., (yield 0.62 gm, 91.7%).

Example 12

N-(4-Methylphenyl)-13-(naphthalen-2-yloxy)propyl] amine [I: $R_1=R_2=R_3=H$, $R_4$=4-methyl phenyl, n=3]

A mixture of anhydrous potassium carbonate (10 gm, in excess) and p-toluedine (0.36 gm, 0.003 mole) was taken in dry DMSO(40 ml).Now 3-(2-naphthyloxy)1-chloropropane (0.5 gm, 0.002 mole) was added in it. Reaction mixture was refluxed at 140° C. for 7 hrs. and the reaction was completed as checked by TLC. Reaction mixture was poured in distilled water (60 ml) and extracted with ethyl acetate thrice. The organic layer was separated and concentrated to get oily compound which was later crystallized by benzene hexane to get (4-methylphenyl)-[3-(naphthylen-2-yloxy)propyl] amine, m.p. 100° C., (yield 0.63 gm, 94.3%).

Example 13

N-(4-Methylphenyl)-[4-(naphthalen-2-yloxy)butyl] amine[I: $R_1=R_2=R_3=H$, $R_4$=4-methyl phenyl, n=4]

A mixture of anhydrous potassium carbonate (10 gm, in excess) and p-toluedine (0.35 gm, 0.003 mole) was taken in dry DMSO(40 ml). Now 4-(2-naphthyloxy)-1-chlorobutane (0.5 gm, 0.002 mole) was added in it. Reaction mixture was refluxed at 150° C. for 8 hrs. and the reaction was completed as checked by TLC. Reaction mixture was poured in distilled water (60 ml) and extracted with ethyl acetate thrice. The organic layer was separated and concentrated to get oily compound which was later crystallized by benzene hexane to get N-(4-methylphenyl)-[4-(naphthalen-2-yloxy)butyl] amine, m.p. 98° C., (yield 0.63 gm, 97%).

Example 14

N-(3-Methoxybenzyl)-[2-napthalen-2-yloxy)ethyl] amine[I: $R_1=R_2=R_3=H$, $R_4$=3-methoxybenzyl, n=2]

A mixture of anhydrous potassium carbonate (10 gm, in excess) and m-methoxy benzyl amine (0.53 gm, 0.003 mole) was taken in dry DMSO (40 ml). Now 2-(2-naphthyloxy)-1-chloroethane (0.5 gm, 0.002 mole) was added in it. Reaction mixture was refluxed at 140° C. for 7 hrs and the reaction was completed as checked by TLC. Reaction mixture was poured in distilled water (60 ml) and extracted with ethyl acetate thrice. The organic layer was separated and concentrated to get oily compound which was later crystallized by benzene hexane to get N-(3-methoxybenzyl)-[2-napthalen-2-yloxy)ethyl]amine, yellow solid, m.p. 93° C., (yield 0.58 gm, 88.6%).

Example 15

N-(3-Methoxybenzyl)-[3-napthalen-2-yloxy)propyl] amine[I: $R_1=R_2=R_3=H$, $R_4$=3-methoxybenzyl, n=3]

A mixture of anhydrous potassium carbonate (10 gm, in excess) and m-methoxy-benzyl amine (0.45 gm, 0.003 mole) was taken in dry DMSO (40 ml). Now 3-(2-naphthyloxy)-1-chloropropane (0.5 gm, 0.002 mole) was added in it. Reaction mixture was refluxed at 150° C. for 8 hrs and the reaction was completed as checked by TLC. Reaction mixture was poured in distilled water (60 ml) and extracted with ethyl acetate thrice. The organic layer was separated and concentrated to get oily compound which was later crystallized by benzene hexane to get N-(3-methoxybenzyl)-[3-napthalen-2-yloxy)propyl]amine yellow, solid, m.p. 97° C., (yield 0.66 gm, 90.6%).

Example 27

N-(3-Methoxybenzyl)-[4-napthalen-2-yloxy)butyl] amine[I: $R_1=R_2=R_3=H$, $R_4$=3-methoxybenzyl, n=4]

A mixture of anhydrous potassium carbonate (10 gm, in excess) and m-methoxy benzyl amine (0.46 gm, 0.003 mole) was taken in dry DMSO (40 ml). Now 4-(2-naphthyloxy)-1-chloropropane (0.5 gm, 0.002 mole) was added in it. Reaction mixture was refluxed at 150° C. for 9 hrs and the reaction was completed as checked by TLC. Reaction mixture was poured in distilled water (60 ml) and extracted with ethyl acetate thrice. The organic layer was separated and concentrated to get oily compound which was later crystallized by benzene hexane to get N-(3-methoxybenzyl)-[4-napthalen-2-yloxy)butyl]amine, yellow solid, m.p. 120° C., (yield 0.68 gm, 94.5%).

Example 17

N-Benzyl-[2-(naphthalen-2-yloxy)-ethyl]amine[I: $R_1=R_2=R_3=H$, $R_4=$benzyl, n=2]

A mixture of anhydrous potassium carbonate (10 gm, in excess) and benzyl amine (0.38 ml, 0.003 mole) was taken in dry DMSO (40 ml). Now 2-(2-naphthyloxy)-1-chloroethane (0.5 gm, 0.002 mole) was added in it. Reaction mixture was refluxed at 140° C. for 7 hrs and the reaction was completed as checked by TLC. Reaction mixture was poured in distilled water (60 ml) and extracted with ethyl acetate thrice. The organic layer was separated and concentrated to get oily compound which was later crystallized by benzene hexane to get N-benzyl-[2-(naphthalen-2-yloxy)-ethyl] amine, solid, m.p. 94° C. (yield 0.61 gm, 90.3%).

Example 18

N-Benzyl-[3-(naphthalen-2-yloxy)-propyl]amine[I: $R_1=R_2=R_3=H$, $R_4=$benzyl, n=3]

A mixture of anhydrous potassium carbonate (10 gm, in excess) and benzyl amine (0.36 ml, 0.003 mole) was taken in dry DMSO (40 ml). Now 3-(2-naphthyloxy)-1-chloropropane (0.5 gm, 0.002 mole) was added in it. Reaction mixture was refluxed at 140° C. for 6 hrs. and the reaction was completed as checked by TLC. Reaction mixture was poured in distilled water (60 ml) and extracted with ethyl acetate thrice. The organic layer was separated and concentrated to get oily compound which was later crystallized by benzene hexane to get N-benzyl-[3-(naphthalen-2-yloxy)-propyl] amine, solid, m.p. 109° C., (yield 0.62 gm, 93.6%).

Example 19

N-Benzyl-[4-(naphthalen-2-yloxy)-butyl]amine[I: $R_1=R_2=R_3=H$, $R_4=$benzyl, n=4]

A mixture of anhydrous potassium carbonate (10 gm, in excess) and benzylamine (0.34 ml, 0.003 mole) was taken in dry DMSO (40 ml). Now 4-(2-naphthyloxy)-1-chlorobutane (0.5 gm, 0.002 mole) was added in it. Reaction mixture was refluxed at 150° C. for 5 hrs. and the reaction was completed as checked by TLC. Reaction mixture was poured in distilled water (60 ml) and extracted with ethyl acetate thrice. The organic layer was separated and concentrated to get oily compound which was later crystallized by benzene hexane to get N-benzyl-[4-(naphthalen-2-yloxy)-butyl]amine, solid, m.p. 105° C., (yield 0.62 gm, 95.3%).

Example 20

N-Cyclohexyl-[2-(naphthalen-2-yloxy)-ethyl]amine [I: $R_1=R_2=R_3=H$, $R_4=$cylohexyl, n=2]

A mixture of anhydrous potassium carbonate (10 gm, in excess) and cyclohexylamine (0.32 ml, 0.003 mole) was taken in dry DMSO (40 ml). Now 2-(2-naphthyloxy)-1-chloro ethane (0.5 gm, 0.002 mole) was added in it. Reaction mixture was refluxed at 140° C. for 7 hrs and the reaction was completed as checked by TLC. Reaction mixture was poured in distilled water (60 ml) and extracted with ethyl acetate thrice. The organic layer was separated and concentrated to get oily compound which was later crystallized by benzene hexane to get N-cyclohexyl-[2-(naphthalen-2-yloxy)-ethyl]amine, solid, m.p. 89° C., (yield 0.56 gm, 85.6%).

Example 21

N-Cyclohexyl-[3-(naphthalen-2-yloxy)-propyl] amine[I: $R_1=R_2=R_3=H$, $R_4=$cylohexyl, n=3]

A mixture of anhydrous potassium carbonate (10 gm, in excess) and cyclohexylamine (0.29 ml, 0.003 mole) was taken in dry DMSO (40 ml). Now 3-(2-naphthyloxy)-1-chloropropane (0.5 gm, 0.002 mole) was added in it. Reaction mixture was refluxed at 140° C. for 7 hrs and the reaction was completed as checked by TLC. Reaction mixture was poured in distilled water (60 ml) and extracted with ethyl acetate thrice. The organic layer was separated and concentrated to get oily compound which was later crystallized by benzene hexane to get N-cyclohexyl-[3-(naphthalen-2-yloxy)-propyl]amine, solid. m.p. 98° C. (yield 0.61 gm, 88%).

Example 22

N-Cyclohexyl-(4-(naphthalen-2-yloxy)-butyl)amine [I: $R_1=R_2=R_3=H$, $R_4=$cylohexyl, n=4]

A mixture of anhydrous potassium carbonate (10 gm, in excess) and cyclohexylamine (0.28 ml, 0.003 mole) was taken in dry DMSO (40 ml). Now 4-(2-naphthyloxy)1-chlorobutane (0.5 gm, 0.002 mole) was added in it. Reaction mixture was refluxed at 150° C. for 5 hrs and the reaction was completed as checked by TLC. Reaction mixture was poured in distilled water (60 ml) and extracted with ethyl acetate thrice. The organic layer was separated and concentrated to get oily compound which was later crystallized by benzene hexane to get N-cyclohexyl-[3-(naphthalen-2-yloxy)-butyl]amine, solid. m.p., 94° C., (yield 0.61 gm, 92%).

Example 23

N-(2-Ethyl-n-hexyl)-(2-(naphthalen-2-yloxy)ethyl) amine[I: $R_1=R_2=R_3=H$, $R_4=$2-ethyl n-hexyl, n=2]

A mixture of anhydrous potassium carbonate (10 gm, in excess) and 2-ethyl n-hexylamine (0.37 ml, 0.003 mole) was taken in dry DMSO(40 ml). Now 2-(2-naphthyloxy)-1-chloroethane (0.5 gm, 0.002 mole) was added in it. Reaction mixture was refluxed at 140° C. for 7 hrs and the reaction was completed as checked by TLC. Reaction mixture was poured in distilled water (60 ml) and extracted with ethyl acetate thrice. The organic layer was separated and concentrated to get oily compound which was later crystallized by benzene hexane to get N-(2-ethyl-n-hexyl)-(2-(naphthalen-2-yloxy)ethyl]amine, solid, m.p. 92° C., (yield 0.62 gm, 83.6%).

Example 24

N-(2-Ethyl-n-hexyl)-(3-(naphthalen-2-yloxy)propyl) amine[I: $R_1=R_2=R_3=H$, $R_4=$2-ethyl-n-hexyl, n=3]

A mixture of anhydrous potassium carbonate (10 gm, in excess) and 2-ethyl-n-hexylamine (0.35 ml, 0.003 mole) was taken in dry DMSO (40 ml). Now 3-(2-naphthyloxy)-1-chloropropane (0.5 gm, 0.002 mole) was added in it. Reaction mixture was refluxed at 140° C. for 7 hrs and the reaction was completed as checked by TLC. Reaction mixture was poured in distilled water (60 ml) and extracted with ethyl acetate thrice. The organic layer was separated and concentrated to get oily compound which was later crystallized by benzene hexane to get N-(2-ethyl-n-hexyl)-(3-(naphthalen-2-yloxy) propyl)amine solid, m.p. 97° C., (yield 0.6 gm, 84.8%).

Example 25

N-(2-Ethyl-n-hexyl)-(4-(naphthalen-2-yloxy)butyl])amine[I: $R_1=R_2=R_3=H$, $R_4$=2-ethyl-n-hexyl, n=4]

A mixture of anhydrous potassium carbonate (10 gm, in excess) and 2-ethyl-n-hexylamine (0.33 ml, 0.003 mole) was taken in dry DMSO (40 ml). Now 4-(2-naphthyloxy)-1-chlorobutane (0.5 gm, 0.002 mole) was added in it. Reaction mixture was refluxed at 140° C. for 7 hrs and the reaction was completed as checked by TLC. Reaction mixture was poured in distilled water (60 ml) and extracted with ethyl acetate thrice. The organic layer was separated and concentrated to get oily compound which was later crystallized by benzene hexane to get N-(2-ethyl-n-hexyl)-(4-(naphthalen-2-yloxy)butyl)amine, solid, m.p. 94° C., (yield 0.61 gm, 87.3%).

Example 26

N-(n-Dodecyl)-(2-(naphthalen-2-yloxy)-ethyl)amine [I: $R_1=R_2=R_3=H$, $R_4$=n-dodecyl, n=2]

A mixture of anhydrous potassium carbonate (10 gm, in excess) and n-dodecylamine (0.55 ml, 0.003 mole) was taken in dry DMSO (40 ml). Now 2-(2-naphthyloxy)-1-chloroethane (0.5 gm, 0.002 mole) was added in it. Reaction mixture was refluxed at 140° C. for 8 hrs and the reaction was completed as checked by TLC. Reaction mixture was poured in distilled water (60 ml) and extracted with ethyl acetate thrice. The organic layer was separated and concentrated to get oily compound which was later crystallized by benzene hexane to get N-(n-dodecyl)-2-(naphthalen-2-yloxy)-ethyl)amine, solid. m.p. 120° C., (yield 0.78 gm, 89.3%)

Example 27

N-(n-Dodecyl)-(3-(naphthalen-2-yloxy)-propyl)amine[I: $R_1=R_2=R_3=H$, $R_4$=n-dodecyl, n=3]

A mixture of anhydrous potassium carbonate (10 gm, in excess) and n-dodecylamine (0.51 ml, 0.003 mole) was taken in dry DMSO (40 ml). Now 3-(2-naphthyloxy)-1-chloropropane (0.5 gm, 0.002 mole) was added in it. Reaction mixture was refluxed at 140° C. for 7 hrs and the reaction was completed as checked by TLC. Reaction mixture was poured in distilled water (60 ml) and extracted with ethyl acetate thrice. The organic layer was separated and concentrated to get oily compound which was later crystallized by benzene hexane to get N-(n-dodecyl)-(3-(naphthalen-2-yloxy)-propyl)amine, solid. m.p. 126° C., (yield 0.78 gm, 92.8%).

Example 28

N-(n-Dodecyl)-[4-(naphthalen-2-yloxy)-butyl]amine [I: $R_1=R_2=R_3=H$, $R_4$=n-dodecyl, n=4]

A mixture of anhydrous potassium carbonate (10 gm, in excess) and n-dodecylamine (0.48 ml, 0.003 mole) was taken in dry DMSO (40 ml). Now 4-(2-naphthyloxy)-1-chlorobutane (0.5 gm, 0.002 mole) was added in it. Reaction mixture was refluxed at 150° C. for 8 hrs and the reaction was completed as checked by TLC. Reaction mixture was poured in distilled water (60 ml) and extracted with ethyl acetate thrice. The organic layer was separated and concentrated to get oily compound which was later crystallized by benzene hexane to get N-(n-dodecyl)-(4-(naphthalen-2-yloxy)-butyl)amine, solid. m.p. 129° C., (yield 0.78 gm, 95.5%).

Example 29

N-(Isoamyl)-(2-(naphthalen-2-yloxy)ethyl)amine[I: $R_1=R_2=R_3=H$, $R_4$=isoamyl, n=2]

A mixture of anhydrous potassium carbonate (10 gm, in excess) and isoamylamine (0.24 ml, 0.003 mole) was taken in dry DMSO (40 ml). Now 2-(2-naphthyloxy)-1-chloroethane (0.5 gm, 0.002 mole) was added in it. Reaction mixture was refluxed at 140° C. for 6 hrs and the reaction was completed as checked by TLC. Reaction mixture was poured in distilled water (60 ml) and extracted with ethyl acetate thrice. The organic layer was separated and concentrated to get oily compound which was later crystallized by benzene hexane to get N-(isoamyl)-(2-(naphthalen-2-yloxy)-ethyl)amine, solid, m.p. 91° C., (yield 0.51 gm, 81%).

Example 30

N-(Isoamyl)-(3-(naphthalen-2-yloxy)-propyl)amine [I: $R_1=R_2=R_3=H$ $R_4$=isoamyl, n=3]

A mixture of anhydrous potassium carbonate (10 gm, in excess) and isoamylamine (0.23 ml, 0.003 mole) was taken in dry DMSO (40 ml). Now 3-(2-naphthyloxy)-1-chloroethane (0.5 gm, 0.002 mole) was added in it. Reaction mixture was refluxed at 150° C. for 5 hrs and the reaction was completed as checked by TLC. Reaction mixture was poured in distilled water (60 ml) and extracted with ethyl acetate thrice. The organic layer was separated and concentrated to get oily compound which was later crystallized by benzene hexane to get isoamyl-[3-(naphthalen-2-yloxy)-propyl]amine, solid, m.p. 95° C., (yield 0.53 gm, 85.6%).

Example 31

N-(Isoamyl)-(4-(naphthalen-2-yloxy)-butyl)amine: $R_1=R_2=R_3=H$, $R_4$=isoamyl, n=4]

A mixture of anhydrous potassium carbonate (10 gm, in excess) and isoamylamine (0.21 ml, 0.003 mole) was taken in dry DMSO (40 ml). Now 4-(2-naphthyloxy)-1-chlorobutane (0.5 gm, 0.002 mole) was added in it. Reaction mixture was refluxed at 140° C. for 7 hrs and the reaction was completed as checked by TLC. Reaction mixture was poured in distilled water (60 ml) and extracted with ethyl acetate thrice. The organic layer was separated and concentrated to get oily compound which was later crystallized by benzene hexane to get N-(isoamyl)-(4-(naphthalen-2-yloxy)-butyl) amine, solid, m.p. 102° C., (yield 0.54 gm, 89.3%).

Example 32

N-(3-Phenylpropyl)-(2-(naphthalen-2-yloxy)ethyl) amine[I:$R_1=R_2=R_3=H$, $R_4$=2-phenylethyl, n=2]

A mixture of anhydrous potassium carbonate (10 gm, in excess) and 3-phenylpropylamine (0.47 ml, 0.003 mole) was taken in dry DMSO (40 ml). Now 2-(2-naphthyloxy)-1-chloroethane (0.5 gm, 0.002 mole) was added in it. Reaction mixture was refluxed at 150° C. for 6 hrs and the reaction was completed as checked by TLC. Reaction mixture was poured in distilled water (60 ml) and extracted with ethyl acetate thrice. The organic layer was separated and concentrated to get oily compound which was later crystallized by benzene hexane to get N-(3-phenylpropyl)-(2-(naphthalen-2-yloxy)ethyl)amine, solid, m.p. 104° C., (yield 0.65 gm, 87.6%).

Example 33

N-(3-Phenylpropyl)-(3-(naphthalen-2-yloxy)propyl) amine[I: $R_1=R_2=R_3=H$, $R_4$=2-phenylethyl, n=3]

A mixture of anhydrous potassium carbonate (10 gm, in excess) and 3-phenylpropylamine (0.44 ml, 0.003 mole) was taken in dry DMSO (40 ml). Now 3-(2-naphthyloxy)-1-chloropropane (0.5 gm, 0.002 mole) was added in it. Reaction mixture was refluxed at 150° C. for 7 hrs and the reaction was completed as checked by TLC. Reaction mixture was poured in distilled water (60 ml) and extracted with ethyl acetate thrice. The organic layer was separated and concentrated to get oily compound which was later crystallized by benzene hexane to get N-(3-phenylpropyl)-(3-(naphthalen-2-yloxy)propyl)amine, solid, m.p. 109° C., (yield 0.645 gm, 89.3%).

Example 34

N-(3-Phenylpropyl)-(4-(naphthalen-2-yloxy)butyl) amine[I: $R_1=R_2=R_3=H$, $R_4$=2-phenylethyl, n=4]

A mixture of anhydrous potassium carbonate (10 gm, in excess) and 3-phenylpropylamine (0.42 ml, 0.003 mole) was taken in dry DMSO (40 ml). Now 4-(2-naphthyloxy)-1-chlorobutane (0.5 gm, 0.002 mole) was added in it. Reaction mixture was refluxed at 145° C. for 7 hrs and the reaction was completed as checked by TLC. Reaction mixture was poured in distilled water (60 ml) and extracted with ethyl acetate thrice. The organic layer was separated and concentrated to get oily compound which was later crystallized by benzene hexane to get N-(3-phenylpropyl)-(4-(naphthalen-2-yloxy)butyl)amine solid, m.p. 117° C., (yield 0.67 gm, 93.6%).

Example 35

N-(n-Octyl)-(2-(napthalen-2-yloxy)ethyl)amine[I: $R_1=R_2=R_3=H$, $R_4$=n-octyl, n=2]

A mixture of anhydrous potassium carbonate (10 gm, in excess) and n-octylamine (0.37 ml, 0.003 mole) was taken in dry DMSO (40 ml). Now 2-(2-naphthyloxy)-1-chloroethane (0.5 gm, 0.002 mole) was added in it. Reaction mixture was refluxed at 140° C. for 7 hrs and the reaction was completed as checked by TLC. Reaction mixture was poured in distilled water (60 ml) and extracted with ethyl acetate thrice. The organic layer was separated and concentrated to get oily compound which was later crystallized by benzene hexane to get N-(n-octyl)-2-(napthalen-2-yloxy)ethylamine, solid, m.p. 105° C., (yield 0.64 gm, 87.6%).

Example 36

N-(n-Octyl)-(3-(napthalen-2-yloxy)propyl)amine[I: $R_1=R_2=R_3=H$, $R_4$=n-octyl, n=3]

A mixture of anhydrous potassium carbonate (10 gm, in excess) and n-octylamine (0.35 ml, 0.003 mole) was taken in dry DMSO (40 ml). Now 3-(2-naphthyloxy)-1-chloropropane (0.5 gm, 0.002 mole) was added in it. Reaction mixture was refluxed at 140° C. for 6 hrs and the reaction was completed as checked by TLC. Reaction mixture was poured in distilled water (60 ml) and extracted with ethyl acetate thrice. The organic layer was separated and concentrated to get oily compound which was later crystallized by benzene hexane to get N-(n-octyl)-(3-(napthalen-2-yloxy)propyl) amine, solid, m.p. 109° C., (yield 0.63 gm, 89%).

Example 37

N-(n-Octyl)-(3-(napthalen-2-yloxy)butyl)amine[I: $R_1=R_2=R_3=H$, $R_4$=n-octyl, n=4

A mixture of anhydrous potassium carbonate (10 gm, in excess) and n-octylamine (0.33 ml, 0.003 mole) was taken in dry DMSO (40 ml). Now 4-(2-naphthyloxy)-1-chlorobutane (0.5 gm, 0.002 mole) was added in it. Reaction mixture was refluxed at 140° C. for 7 hrs and the reaction was completed as checked by TLC. Reaction mixture was poured in distilled water (60 ml) and extracted with ethyl acetate thrice. The organic layer was separated and concentrated to get oily compound which was later crystallized by benzene hexane to get N-(n-octyl)-(3-(napthalen-2-yloxy)butyl) amine, solid, m.p 114° C., (yield 0.65 gm, 93.4%).

Example 38

N-(n-Butyl)-(4-(naphthalen-2-yloxy)butyl)amine[I: $R_1=R_2=R_3=H$, $R_4$=n-butyl, n=4]

A mixture of anhydrous potassium carbonate (10 gm, in excess) and n-butylamine (0.32 ml, 0.003 mole) was taken in dry DMSO (40 ml). Now 4-(2-naphthyloxy)-1-chlorobutane (0.5 gm, 0.002 mole) was added in it. Reaction mixture was refluxed at 140° C. for 8 hrs and the reaction was completed as checked by TLC. Reaction mixture was poured in distilled water (60 ml) and extracted with ethyl acetate thrice. The organic layer was separated and concentrated to oily compound which was later crystallized by benzene hexane to get N-(n-butyl)-(4-(naphthalen-2-yloxy)butyl) amine, solid. m.p. oil, (yield 0.56 gm, 96.5%).

Example 39

N-(n-Propyl)-(4-(naphthalen-2-yloxy)butyl)amine[I: $R_1=R_2=R_3=H$, $R_4$=n-propyl, n=4]

A mixture of anhydrous potassium carbonate (10 gm, in excess) and n-propyl amine (0.26 ml, 0.003 mole) was taken in dry DMSO (40 ml). Now 4-(2-naphthyloxy)-1-chlorobutane (0.5 gm, 0.002 mole) was added in it. Reaction mixture was refluxed at 140° C. for 7 hrs and the reaction was completed as checked by TLC. Reaction mixture was poured in distilled water (60 ml) and extracted with ethyl acetate thrice. The organic layer was separated and concentrated to oily compound which was later crystallized by benzene hexane to get N-(n-propyl)-(4-(naphthalen-2-yloxy)butyl) amine, solid, m.p. 118° C., (yield 0.51 gm, 93.2%).

Example 40

N-(2-Phenylethyl)-(2-(naphthalen-2-yloxy)butyl) amine[I, $R_1=R_2=R_3=H$, $R_4$=2-phenylethyl, n=4]

A mixture of anhydrous potassium carbonate (10 gm, in excess) and phenylethylamine (0.4 ml, 0.003 mole) was taken in dry DMSO (40 ml). Now 4-(2-naphthyloxy)-1-chlorobutane (0.5 gm, 0.002 mole) was added in it. Reaction mixture was refluxed at 140° C. for 8 hrs and the reaction was completed as checked by TLC. Reaction mixture was poured in distilled water (60 ml) and extracted with ethyl acetate thrice. The organic layer was separated and concentrated to oily compound which was later crystallized by benzene hexane to get N-(2-phenylethyl)-(2-(naphthalen-2-yloxy)butyl)amine, solid, m.p. 139° C., (yield 0.656 gm, 95.6%).

Example 41

N-(Piperidinyl-(4-(naphthalen-2-yloxy)butyl)amine [I: $R_1=R_2=R_3=H$, $R_4$=piperidinyl, n=4]

A mixture of anhydrous potassium carbonate (10 gm, in excess) and piperidine (0.32 ml, 0.003 mole) was taken in dry DMSO (40 ml). Now 4-(2-naphthyloxy)-1-chlorobutane (0.5 gm, 0.002 mole) was added in it. Reaction mixture was refluxed at 150° C. for 7 hrs. and the reaction was completed as checked by TLC. Reaction mixture was poured in distilled water (60 ml) and extracted with ethyl acetate thrice. The organic layer was separated and concentrated to oily compound which was latter crystallized by benzene hexane to get N-(piperidinyi)-(4-(naphthalen-2-yloxy)butyl)amine, oil, (yield 0.54 gm, 88.6%).

Example 42

N-(n-Butyl)-(3-(naphthalen-2-yloxy)propyl)amine[I, $R_1=R_2=R_3=H$, $R_4$=n-butyl, n=3]

A mixture of anhydrous potassium carbonate (10 gm, in excess) and n-butylamine (0.34 ml, 0.003 mole) was taken in dry DMSO (40 ml). Now 3-(2-naphthyloxy)-1-chloropropane (0.5 gm, 0.002 mole) was added in it. Reaction mixture was refluxed at 135° C. for 7 hrs and the reaction was completed as checked by TLC. Reaction mixture was poured in distilled water (60 ml) and extracted with ethyl acetate thrice. The organic layer was separated and concentrated to get oily compound which was later crystallized by benzene hexane to get N-(n-butyl)-(3-(naphthalen-2-yloxy)propyl) amine, solid, m.p. 112° C., (yield 0.55 gm, 94.5%).

Example 51

N-(n-Propyl)-(3-(naphthalen-2-yloxy)propyl)amine [I, $R_1=R_2=R_3=H$, $R_4$=n-propyl, n=3]

A mixture of anhydrous potassium carbonate (10 gm, in excess) and n-propylamine (0.28 ml, 0.003 mole) was taken in dry DMSO (40 ml). Now 3-(2-naphthyloxy)-1-chloropropane (0.5 gm, 0.002 mole) was added in it. Reaction mixture was refluxed at 145° C. for 8 hrs and the reaction was completed as checked by TLC. Reaction mixture was poured in distilled water (60 ml) and extracted with ethyl acetate thrice. The organic layer was separated and concentrated to get oily compound which was later crystallized by benzene hexane to get N-(n-propyl-(3-(naphthalen-2-yloxy)propyl) amine, solid, m.p. 112° C., (yield 0.51 gm, 91.2%).

Example 44

N-(2-Phenylethyl)-(3-(naphthalen-2-yloxy)propyl) amine[I, $R_1=R_2=R_3=H$, $R_4$=2-phenylethyl, n=3]

A mixture of anhydrous potassium carbonate (10 gm, in excess) and 2-phenylethylamine (0.51 ml, 0.003 mole) was taken in dry DMSO (40 ml). Now 3-(2-naphthyloxy)-1-chloropropane (0.5 gm, 0.002 mole) was added in it. Reaction mixture was refluxed at 145° C. for 7 hrs and the reaction was completed as checked by TLC. Reaction mixture was poured in distilled water (60 ml) and extracted with ethyl acetate thrice. The organic layer was separated and concentrated to get oily compound which was later crystallized by benzene hexane to get N-(2-phenylethyl)-(3-(naphthalen-2-yloxy)propyl)amine, solid, m.p. 270° C., (yield 0.65 gm, 93.7%).

Example 45

N-(Piperidinyl)-(3-(naphthalen-2-yloxy)propyl) amine[I, $R_1=R_2=R_3=H$, $R_4$=Piperidinyl, n=3]

A mixture of anhydrous potassium carbonate (10 gm, in excess) and piperidine (0.34 ml, 0.003 mole) was taken in dry DMSO (40 ml). Now 3-(2-naphthyloxy)-1-chloropropane (0.5 gm, 0.002 mole) was added in it. Reaction mixture was refluxed at 150° C. for 8 hrs. and the reaction was completed as checked by TLC. Reaction mixture was poured in distilled water (60 ml) and extracted with ethyl acetate thrice. The organic layer was separated and concentrated to get oily compound which was later crystallized by benzene hexane to get N-(piperidinyl)-(3-(naphthylan-2-yloxy)propyl)amine, solid, m.p. 78° C., (yield 0.53 gm, 85.7%).

Example 46

N-(4-Methoxyphenyl)-N-methyl[3-(naphthalen-2-yloxy)propyl amine.[I, $R_1=R_2=H$, $R_3$=methyl, $R_4$=4-methoxyphenyl, n=3]

A mixture of (4-methoxyphenyl)-[3-(naphthalen-2-yloxy) propyl]amine (0.5 gm, 0.002 mole) and methyl iodide (0.49 ml, 0.003 mole) was taken in dry acetone (40 ml). It was refluxed for 12 hrs and the progress of reaction checked by TLC. Reaction mixture was filtered and the filtrate was concentrated to get oily compound which was further crystallized by benzene hexane mixture to get N-(4 methoxyphenyl)-N-methyl (3-(naphthalen-2-yloxy)propyl) amine, crystallized as yellow solid, m.p. 112° C., (yield 0.69 gm, 94%)

Example 47

N-(4 Methoxyphenyl)-N-ethyl(3-(naphthalen-2-yloxy)propyl)amine.[I, $R_1=R_2=H$, $R_3=$ethyl, $R_4=$4-methoxyphenyl, n=3]

A mixture of N-(4-methoxyphenyl)-[3-(naphthalen-2-yloxy)propyl]amine (0.5 gm, 0.002 mole) and ethyl bromide (0.52 ml, 0.003 mole) was taken in dry acetone (40 ml). It was refluxed for 12 hrs and the progress of reaction checked by TLC. Reaction mixture was filtered and the filtrate was concentrated to get oily compound which was further crystallized by benzene hexane mixture to get N-(4 methoxyphenyl)-N-ethyl [3-(naphthalen-2-yloxy)propylamine, crystallized as yellow oil, (yield 0.64 gm, 94.6%).

Example 49

N-(4-Methoxyphenyl)-N-propyl[3-(naphthalen-2-yloxy)propylamine[I, $R_1=R_2=H$, $R_3=$propyl, $R_4=$4-methoxyphenyl, n=3]

A mixture of N-(4-methoxyphenyl)-[3-(naphthalen-2-yloxy)propyl]amine (0.5 gm, 0.002 mole) and propyl bromide (0.54 ml, 0.003 mole) was taken in dry acetone (40 ml). It was refluxed for 12 hrs and the progress of reaction checked by TLC. Reaction mixture was filtered and the filtrate was concentrated to get oily compound which was further crystallized by benzene hexane mixture to get N-(4-methoxyphenyl)-N-propyl[3-(naphthalen-2-yloxy)propylamine, crystallized yellow solid, m.p. 127° C., (yield 0.67 gm, 95.7%)

Example 50

N-(4-Methoxyphenyl)-N-butyl-(3-(naphthalen-2-yloxy)propyl)amine[I, $R_1=R_2=H$, $R_3=$n-butyl, $R_4=$4-Methoxyphenyl, n=3]

A mixture of N-(4-methoxyphenyl)-(3-(naphthalen-2-yloxy)propyl)amine (0.5 gm, 0.002 mole) and butyl iodide (1 ml, 0.003 mole) was taken in dry acetone (40 ml). It was refluxed for 12 hrs and the progress of reaction checked by TLC. Reaction mixture was filtered and the filtrate was concentrated to get oily compound which was further crystallized by benzene hexane mixture to get N-(4-methoxyphenyl)-N-butyl-(3-(naphthalen-2-yloxy) propyl) amine crystallized yellow solid, m.p. 127° C., (yield 0.78 gm, 98%).

Example 51

{N-(4-Methoxyphenyl)-(3-(naphthalen-2-yloxy)propyl)amino}acetic acid ethyl ester[I, $R_1=R_2=H$, $R_3=$—$CH_2COOEt$, $R_4=$4-Methoxyphenyl, n=3]

A mixture of (4-methoxyphenyl)-(3-(naphthalen-2-yloxy) propyl)amine (0.5 gm, 0.002 mole) and ethyl bromoacetate (0.62 ml, 0.003 mole) was taken in dry acetone (40 ml). It was refluxed for 10 hrs and the progress of reaction checked by TLC. Reaction mixture was filtered and the filtrate was concentrated to get the oily compound {N-(4-methoxy phenyl)-(3-(naphthalen-2-yloxy)propyl)amino}acetic acid ethyl ester, oil (yield 0.75 ml, 96%).

Example 52

2,7-Bis[3-(4-methoxyphenylamino)propyloxy]naphthalene[I, $R_1=$4-methoxyphenyl amino propyloxy, $R_2$ & $R_3=$H, $R_4=$4-methoxyphenyl]

A mixture of 2,7-bis(3-chloropropyloxy)naphthalene (1 gm, 0.003 mole) and p-anisidine (1.17 gm, 0.005 mole) were taken in 60 ml dry DMSO. It was refluxed at 140° C. for 12 hrs the completion of the reaction was checked by TLC. The reaction mixture was poured into distilled water (80 ml) and extracted with ethyl acetate thrice. The organic layer was separated and concentrated to get oily compound which was further crystallized by benzene hexane to get the desired compound as solid, m.p. 127° C., (yield 1.34 gm, 89%).

Example 53

2,6-Bis[3-(4-methoxyphenylamino)propyloxy]naphthalene[I, $R_2=$4-methoxyphenyl amino propyloxy, $R_1$ & $R_3=$H, $R_4=$4-methoxyphenyl]

A mixture of 2,6-bis(3-chloropropyloxy)naphthalene(1 gm, 0.003 mole) and p-anisidine(1.17 gm, 0.005 mole) was taken in 60 ml dry DMSO. It was refluxed at 140° C. for 12 hrs. The completion of the reaction was checked by TLC. The reaction mixture was poured into distilled water (80 ml) and extracted with ethyl acetate thrice. The organic layer was separated and concentrated to get oily compound which was further crystallized by benzene hexane to get the desired compound, m.p. 129° C., (yield 1.4 gm, 91%).

Biological Activity

A Antidiabetic Activity

Animals:

Adult male and female albino rats (Sprague Dawley) of body weight 160±20 g, bred in CDRI animal house were used during the course of experiment; 6 animals were kept in one cage. All-the animals were fed ad-lib standard pellet diet (Lipton, Bombay) and allowed unrestricted access to water. The following norms were followed for animal room environment. Temperature: 22±1° C.; Humidity: 50—50%; Light 300 Lux at floor level with regular 12 hours light cycle; noise level 50 decibels; ventilation 10–50 air changes per hour.

The blood-glucose lowering effects of the test samples/standard drugs were examined in the following two experimental models.

Sucrose-Loaded Rat Model:

Overnight fasted male Sprague Dawley rats were used for the sucrose-loaded experiment. Blood was collected at '0' min from the tail vein of the animals. After the '0' min blood collection, samples/drugs were given to the test group consisting of 5 rats by oral gavage at a dose of 100 mg/kg. Half an hour post test sample treatment, a sucrose-load of 10.0 gm/kg body weight was given to each rat. The blood was collected at 30, 60, 90 & 120 min post sucrose-load.

Streptozotocin-Induced Diabetic Rat Model:

Single-dose effect; Sprague Dawley strain male albino rats of average body weight 160±20 g were selected for this study. A calculated amount of the fresh solution of STZ dissolved in 100 mM citrate buffer (ph 4.5) was injected to overnight fasted rats (60 mg/Kg) intraperitoneally. Blood was checked for glucose content 48 h later by glucometer & animals showing blood glucose profile above 250 mg/dl were selected and were divided into different groups. Blood-glucose levels were again tested at 1, 2, 3, 4, 5, 6, 7 and 24 h post test sample/drug administration. Food but not water was withdrawn from the cages during the experiment.

Sucrose Challenged Streptozotocin-Induced Diabetic Rat Model:

Single-dose effect; Sprague Dawley strain male albino rats of average body weight 160±20 g were selected for this study. A calculated amount of the fresh solution of STZ dissolved in 100 mM citrate buffer (ph 4.5) was injected to overnight fasted rats (60 mg/Kg) intraperitoneally. Blood was checked for glucose content 48 h later by glucometer & animals showing blood glucose profile between 150–250 mg/dl were selected and were divided into different groups. Half an hour post test sample treatment, a sucrose-load of 2.5 g/kg body weight was given to each rat. Blood-glucose levels were again tested at 30, 60, 90, 120, 180, 240, 300 min and 24 h post test sample/drug administration. Food but not water was withdrawn from the cages during the experiment.

(1) Hypoglycaemic Activity of Test Compounds (Compound No. 1 and 4), Glybenclamide and Gliclazide in Normal Rats:

The antidiabetic effect of test compounds (compound no. 1 and 4) and standard drug Glybenclamide, Gliclazide on OGTT of normal rats was determined. At 100-mg/kg doses level, test compounds 1,4, Glybenclamide and Gliclazide showed significant lowering 33.6%, 37.6%, 33.9% and 44.8% respectively, at 120 min post glucose load.

2) Hypoglycaemic Activity of Example 1, Glybenclamide and Gliclazide in STZ-Induced Diabetic Rats:

The effect of Test compound 1 and standard antidiabetic drug Glybenclamide and gliclazide on blood glucose lowering in STZ-induced diabetic rats were determined. At 100 mg/kg dose level compound 1, Glybenclamide and gliclazide showed significant lowering on blood glucose. The lowering started from 1-hour that persisted up to 7-hours post drug administration. The lowering was of the order 28.0%, 32.8% and 27.7% respectively in case of test compound 1, Glybenclamide and gliclazide.

B. Lipid Lowering Activity

Lipid lowering activity of compound-1 was evaluated in two different models in vivo.

(a)Triton Model: Male Charles foster rats weighing 200–225 g were divided into control, hyperlipedemic and hyperlipedemic plus drug treated groups containing six animals each. Hyperlipedemia was induced by administration of triton WR-1339(400 mg/kg,IP). All animals were maintained on standard pellet diet and water ad lib. Test compound no. 1 and Gugulipid (standard drug) were macerated with 2% aqueous gum acacia and this suspension was fed orally at the dose of 100 mg/kg simultaneously with triton. The animals of control group received same amount of gum acacia. At the end of experiment, after 18 hrs, blood was withdrawn from retro orbital plexus and plasma was used for the assay of total cholesterol, phospholipid and triglyceride by standard spectrophotometric method.

Results: Administration of triton in rats produced marked hyperlipedemia as observed by the increased levels of plasma cholesterol, phospholipid and triglyceride by 2.92, 3.32, 3.64 folds respectively (Table-1).

Treatment with compound-1 and gugulipid significantly lowered the plasma levels of cholesterol, phospholipid and triglyceride by 26,33 and 28% as well as 35, 31, and 35% respectively in triton plus drug treated groups.

TABLE 1

Lipid lowering activity of test compound 1 (% lowering of plasma lipids)

| Entry No. | Cholesterol | Phospholipid | Triglyceride |
|---|---|---|---|
| Test Compound 1 | 26* | 33** | 28* |
| Gugulipid (standard drug) | 35** | 31** | 35** |

*p < 0.01,
**<0.001 as compared to hyperlipemic group (b) Dyslipemic Hamster Model: Male golden syrian hamster weighing 120–130 gm were divided into control, dyslipemic and dyslipemic plus drug treated group of 8 animals in each.

Dyslipemia was produced by feeding with fructose rich high fat diet(HFD). Dyslipemic hamsters had free acccess to HFD and water ad. Lib for 10 days (day 1 to day 10). Compound 1 was macerated in vehicle containing 0.2% CMC+0.4% tween-80 in distilled water and fed orally at the dose of 300□ mole/kg from day 4 to day 10 simultaneously with HFD feeding to hamster. Control animals received same amount of vehicle. At the end of the experiment on $10^{th}$ day, blood was withdrawn and plasma was used for assay of triglyceride(Tg), cholesterol(chol), high density lipoprotein (HDL), glucose, glycerol and free fatty acids(FFA) by standard spectrophotometric methods on auto analyser. In another set of experiment antidyslipemic activity of fenofibrate at the dose of 1000□ mole/kg was evaluated.

Results: Feeding with HFD produced marked dyslipemia in hamsters. Plasma level of Tg, chol, glycerol and FFA were shown to increase by 800, 214, 167 and 215% respectively followed by a significant increase in the levels of glucose and HDL by 116 and 19% respectively. Feeding with test compound reduced levels of plasma Tg, chol, glycerol, HDL and glucose by 48, 8, 14, 15 and 31% respectively. No significant change in FFA levels was observed. Similarly in another experiment with finofibrate (standard drug), the lowering in plasma, Tg, chol, glucose, glycerol and FFA was 77, 30, 33, 52 and 53% respectively followed by 33% increase in plasma HDL in HFD fed dyslipemic hamsters.

TABLE 2

Activity profile of Test compound 1(per cent change in lipid biochemical parameters)

| Compound | Dose (µmol/kg) | TG | CHOL | HDL | GLU | GLY | FFA |
|---|---|---|---|---|---|---|---|
| Test Compound1 | 300 | −48** | −8 | +15 | −31** | −14 | NC |
| Fenofibrate (standard drug) | 1000 | −77** | −30** | +33** | −33** | −52** | −53** |

**p value < 0.001, values are mean + sd of 8 animals

These results show that the test compound 1 besides having sugar lowering activity, has the added advantage of antihyperlipedemic activity as well.

We claim:
1. An ω-naphthyloxy amino alkane compound having structural formula I,

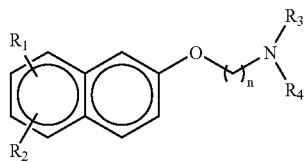

wherein $R_1$ and $R_2$ are individually H, a lower alkyl containing 1–6 carbon atoms selected from the group consisting of methyl, ethyl, propyl, butyl, pentyl and hexyl; a branched chain lower alkyl selected from the group consisting of isopropyl, isobutyl, t-butyl and alkyl chains thereof; a cyclic alkane selected from the group consisting of cyclopropyl, cyclobutyl, cyclohexyl, cycloheptyl and cyclic alkanes thereof; a lower alkoxy in which the alkyl group is as mentioned above, n is 1 to 6; $R_3$ and $R_4$ are individually H, a lower straight or branched chain alkyl containing 1–15 carbon atoms as mentioned above; a cyclic alkane as defined above; an aryl residue selected from the group consisting of phenyl and naphthyl; an arylalkyl residue selected from the group consisting of benzyl and substituted benzyl, form a part of a heterocylic ring selected from the group consisting of pyrrolidine and piperidine, form a heterocylic ring with additional heteroatoms O, N, S, selected from the group consisting of piperazine, morpholine, oxazole, oxathiazole and oxathiazine; an alkoxy carbonyl alkane represented by the formula $R_6COOR_7$, wherein $R_6$ is $(CH_2)n$ (n=1–3) and $R_7$ is a lower alkyl as defined above, provided that either $R_1$ and $R_2$ or $R_3$ and $R_4$ are not both H.

2. The ω-naphthyloxy amino alkane compound as claimed in claim 1, selected from the group consisting of:
(i) N-(4-Methoxyphenyl)-[3-(naphthalen-2-yloxy)propyl] amine [I: $R_1=R_2=R_3=H$, $R_4$=4-methoxyphenyl, n=3]
(ii) N-(4-Methoxyphenyl)-N-propyl[3-(naphthalen-2-yloxy)propyl] amine [I: $R_1=R_2=H$, $R_3$=propyl $R_4$=4-methoxyphenyl, n=3]
(iii) N-(4-Methoxyphenyl)-[3-(naphthalen-2-yloxy)propyl] amino acetic acid ethyl ester [I: $R_1=R_2=H$, $R_3=CH_2COOEt$, $R_4$=4-methoxy phenyl, n=3]
(iv) N-Benzyl-[2-(naphthalen-2-yloxy)-ethyl]amine [I: $R_1=R_2=R_3=H$, $R_4$=benzyl, n=2]
(v) N-(4-Methoxyphenyl)-[2-(naphthalen-2-yloxy)ethyl] amine [I: $R_1=R_2=R_3=H$, $R_4$=4-methoxyphenyl, n=2]
(vi) N-(4-Methoxyphenyl)-[3-(naphthalen-2-yloxy)propyl] amine [I: $R_1=R_2=R_3=H$, $R_4$=4-methoxy phenyl, n=3]
(vii) N-(4-Methoxyphenyl)-[4-(naphthalen-2-yloxy)butylamine [I: $R_1=R_2=R_3=H$, $R_4$=4-methoxyphenyl, n=4]
(viii) N-(4-Methylphenyl)-[2-(naphthalen-2-yloxy)ethyl] amine [I: $R_1=R_2=R_3=H$, $R_4$=4-methylphenyl, n=2]
(ix) N-(4-Methylphenyl)-[3-(naphthalen-2-yloxy)propyl] amine [I: $R_1=R_2=R_3=H$, $R_4$=4-methylphenyl, n=3]
(x) N-(4-Methylphenyl)-[4-(naphthalen-2-yloxy)butyl] amine [I: $R_1=R_2=R_3=H$, $R_4$=4-methyl phenyl, n=4]
(xi) N-(3-Methoxybenzyl)-[2-napthalen-2-yloxy)ethyl] amine [I: $R_1=R_2=R_3=H$, $R_4$=3-methoxy benzyl, n=2]
(xii) N-(3-Methoxybenzyl)-[3-napthalen-2-yloxy)propyl] amine [I: $R_1=R_2=R_3=H$, $R_4$=3-methoxybenzyl, n=3]
(xiii) N-(3-Methoxybenzyl)-[4-napthalen-2-yloxy)butyl] amine [I: $R_1=R_2=R_3=H$, $R_4$=3-methoxybenzyl, n=4]
(xiv) N-Benzyl-[2-(naphthalen-2-yloxy)-ethyl] amine [I: $R_1=R_2=R_3=H$, $R_4$=benzyl, n=2]
(xv) N-Benzyl-[3-(naphthalen-2-yloxy)-propyl] amine [I: $R_1=R_2=R_3=H$, $R_4$=benzyl, n=3]
(xvi) N-Benzyl-[4-(naphthalen-2-yloxy)-butyl] amine [I: $R_1=R_2=R_3=H$, $R_4$=benzyl, n=4]
(xvii) N-Cyclohexyl-[2-(naphthalen-2-yloxy)-ethyl] amine [I: $R_1=R_2=R_3=H$, $R_4$=cyclohexyl, n=2]
(xviii) N-Cyclohexyl-[3-(naphthalen-2-yloxy)propyl] amine [I: $R_1=R_2=R_3=H$, $R_4$=cyclohexyl, n=3]
(xix) N-Cyclohexyl-[4-(naphthalen-2-yloxy)-butyl] amine [I: $R_1=R_2=R_3=H$, $R_4$=cyclohexyl, n=4]
(xx) N-(2-Ethyl-n-hexyl)-[2-(naphthalen-2-yloxy)ethyl] amine [I: $R_1=R_2=R_3=H$, $R_4$=2-ethyl n-hexyl, n=2]
(xxi) N-(2-Ethyl-n-hexyl)-[3-(naphthalen-2-yloxy)propyl] amine [I: $R_1=R_2=R_3=H$, $R_4$=2-ethyl-n-hexyl, n=3]
(xxii) N-(2-Ethyl-n-hexyl)-[4-(naphthalen-2-yloxy)butyl] amine [I: $R_1=R_2=R_3=H$, $R_4$=2-ethyl-n-hexyl, n=4]
(xxiii) N-(n-Dodecyl)-[2-(naphthalen-2-yloxy)-ethyl] amine [I: $R_1=R_2=R_3=H$, $R_4$=n-dodecyl, n=2]
(xxiv) N-(n-Dodecyl)-[3-(naphthalen-2-yloxy)-propyl] amine [I: $R_1=R_2=R_3=H$, $R_4$=n-dodecyl, n=3]
(xxv) N-(n-Dodecyl)-[4-(naphthalen-2-yloxy)-butyl] amine [I: $R_1=R_2=R_3=H$, $R_4$=n-dodecyl, n=4]
(xxvi) N-(Isoamyl)-[2-(naphthalen-2-yloxy)-ethyl] amine [I: $R_1=R_2=R_3=H$, $R_4$=isoamyl, n=2]
(xxvii) N-(Isoamyl)-[3-(naphthalen-2-yloxy)-propyl] amine [I: $R_1=R_2=R_3=H$ $R_4$=isoamyl, n=3]
(xxviii) N-(Isoamyl)-[4-(naphthalen-2-yloxy)-butyl] amine [I: $R_1=R_2=R_3=H$, $R_4$=isoamyl, n=4]
(xxix) N-(3-Phenylpropyl)-[2-(naphthalen-2-yloxy)ethyl] amine [I: $R_1=R_2=R_3=H$, $R_4$=2-phenyl ethyl, n=2]
(xxx) N-(3-Phenylpropyl)-[3-(naphthalen-2-yloxy)propyl] amine [I: $R_1=R_2=R_3=H$, $R_4$=2-phenylethyl, n=3]
(xxxi) N-(3-Phenylpropyl)-[4-(naphthalen-2-yloxy)butyl] amine [I: $R_1=R_2=R_3=H$, $R_4$=2-phenylethyl, n=4]
(xxxii) N-(n-Octyl)-[2-(naphthalen-2-yloxy)ethyl] amine [I: $R_1=R_2=R_3=H$, $R_4$=n-octyl, n=2]
(xxxiii) N-(n-Octyl)-[3-(naphthalen-2-yloxy)propyl] amine [I: $R_1=R_2=R_3=H$, $R_4$=n-octyl, n=3]
(xxxiv) N-(n-Octyl)-[3-(napthalen-2-yloxy)butyl] amine [I: $R_1=R_2=R_3=H$, $R_4$=n-octyl, n=4]
(xxxv) N-(n-Butyl)-[4-(naphthalen-2-yloxy)butyl] amine [I: $R_1=R_2=R_3=H$, $R_4$=n-butyl, n=4]
(xxxvi) N-(n-Propyl)-[4-(naphthalen-2-yloxy)butyl] amine [I: $R_1=R_2=R_3=H$, $R_4$=n-propyl, n=4]
(xxxvii) N-(2-Phenylethyl)-[2-(naphthalen-2-yloxy)butyl] amine [I: $R_1=R_2=R_3=H$, $R_4$=2-phenyl-ethyl, n=4]
(xxxviii) N-(Piperidinyl)-[4-(naphthalen-2-yloxy)butyl] amine [I: $R_1=R_2=R_3=H$, $R_4$=Piperidinyl, n=4]
(xxxix) N-(n-Butyl)-[3-(naphthalen-2-yloxy)propyl] amine [I: $R_1=R_2=R_3=H$, $R_4$=n-butyl, n=3]
(xl) N-(n-Propyl)-[3-(naphthalen-2-yloxy)propyl] amine [I: $R_1=R_2=R_3=H$, $R_4$=n-propyl, n=3]

(xli) N-(2-Phenylethyl)-[3-(naphthalen-2-yloxy)propyl] amine [I: $R_1=R_2=R_3=H$, $R_4=$2-phenylethyl, n=3]

(xlii) N-(Piperidinyl)-[3-(naphthalen-2-yloxy)propyl] amine [I: $R_1=R_2=R_3=H$, $R_4=$Piperidinyl, n=3]

(xliii) N-(4-Methoxyphenyl)-N-methyl[3-(naphthalen-2-yloxy)propyl] amine [I: $R_1=R_2=H$, $R_3=$methyl, $R_4=$4-methoxyphenyl, n=3]

(xliv) N-(4 Methoxyphenyl)-N-ethyl[3-(naphthalen-2-yloxy)propyl] amine [I: $R_1=R_2=H$, $R_3=$ethyl, $R_4=$4-methoxyphenyl, n=3]

(xlv) N-(4-Methoxyphenyl)-N-propyl[3-(naphthalen-2-yloxy)propyl] amine [I: $R_1=R_2=H$, $R_3=$propyl, $R_4=$4-methoxyphenyl, n=3]

(xlvi) N-(4-Methoxyphenyl)-N-butyl[3-(naphthalen-2-yloxy)propyl] amine[I: $R_1=R_2=H$, $R_3=$n-butyl, $R_4=$4-methoxyphenyl, n=3]

(xlvii) N-(4-Methoxyphenyl)-[3-(naphthalen-2-yloxy) propyl]amino acetic acid ethyl ester[I: $R_1=R_2=H$, $R_3=-CH_2COOEt$, $R_4=$4-methoxyphenyl, n=3]

(xlviii) 2,7-Bis[3-(4methoxyphenylamino)propyloxy] naphthalene [I: $R_1=$4-methoxyphenyl amino propyloxy, $R_2$ & $R_3=H$, $R_4=$4-methoxyphenyl] and (xlix) 2,6-Bis[3-(4-methoxyphenylamino)propyloxy] naphthalene [I: $R_2=$4-methoxyphenyl amino propyloxy, $R_1$ & $R_3=H$, $R_4=$4-methoxyphenyl].

3. The ω-naphthyloxy amino alkane compound as claimed in claim 1, wherein said compound is useful for treatment of hyperglycemia and cardiovascular disorders (CVS) in mammals, including humans.

4. The ω-naphthyloxy amino alkane compound as claimed in claim 1, wherein the said compound is administered as a pharmaceutical composition optionally along with a pharmaceutically acceptable salt, carrier or dilutent.

5. The ω-naphthyloxy amino alkane compound as claimed in claim 4, wherein the salt, carrier or diluent is selected from a group of lactose, sodium chloride, potassium chloride, magnesium sulphate, magnesium chloride, potassium sulfate, sodium sulfate, lithium sulphate, sodium phosphate, potassium phosphate, magnesium succinate, sodium carbonate, sodium sulfate, potassium acid phosphate calcium bicarbonate.

6. The ω-naphthyloxy amino alkane compound as claimed in claim 1 wherein the dosage of the said compound is in the range of about 250–350 µmol/Kg.

7. The ω-naphthyloxy amino alkane as claimed in claim 6 wherein, the dosage of the said compound is about 300 µmol/Kg.

8. The ω-naphthyloxy amino alkane compound as claimed in claim 1, wherein said compound is administered in the form of a syrup, a capsule, a tablet, an intravenous preparation, a liquid or a suspension.

9. The ω-naphthyloxy amino alkane compound as claimed in claim 1, wherein the compound is administered orally, intranasally, rectally, or parenterally.

10. The ω-naphthyloxy amino alkane compound as claimed in claim 1, wherein said compound lowers plasma concentration of cholesterol by about 30%.

11. The ω-naphthyloxy amino alkane compound as claimed in claim 10, wherein said compound lowers plasma concentration of cholesterol preferably by about 26%.

12. The ω-naphthyloxy amino alkane compound as claimed in claim 1 wherein said compound lowers plasma concentration of phospholipids by about 35%.

13. The ω-naphthyloxy amino alkane compound as claimed in claim 12, wherein said compound lowers plasma concentration of phospholipids preferably by about 30%.

14. The ω-naphthyloxy amino alkane compound as claimed in claim 1 wherein said compound lowers plasma concentration of triglyceride by about 50%.

15. The ω-naphthyloxy amino alkane compound as claimed in claim 14 wherein said compound lowers plasma concentration of triglyceride preferably by about 48%.

16. The ω-naphthyloxy amino alkane compound as claimed in claim 1 wherein said compound enhances plasma concentration of high-density lipoproteins (HDL) by about 20%.

17. The ω-naphthyloxy amino alkane compound as claimed in claim 16 wherein said compound enhances plasma concentration of high-density lipoproteins (HDL) by about 15%.

18. The ω-naphthyloxy amino alkane compound as claimed in claim 1 wherein said compound lowers plasma glucose (GLU) concentration by about 35%.

19. The ω-naphthyloxy amino alkane compound as claimed in claim 18 wherein said compound lowers plasma glucose concentration preferably by about 30%.

20. The ω-naphthyloxy amino alkane compound as claimed in claim 1 wherein said compound lowers plasma glycerol (GLY) concentration by about 20%.

21. The ω-naphthyloxy amino alkane compound as claimed in claim 1 wherein said compound lowers plasma glycerol (GLY) concentration preferably by about 14%.

22. The ω-naphthyloxy amino alkane compound as claimed in claim 1 wherein said compound lowers plasma glucose concentration in about 30 min to 10 hours post administration.

23. The ω-naphthyloxy amino alkane compound as claimed in claim 22 wherein, the compound lowers plasma glucose concentration in about 1 hr to 7 hrs post administration.

24. A method for preparing an ω-naphthyloxy amino alkane compound having structural formula I,

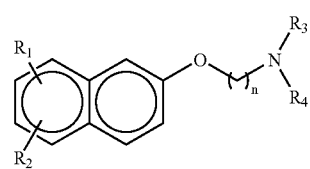

wherein $R_1$ and $R_2$ are individually H, a lower alkyl containing 1–6 carbon atoms selected from the group consisting of methyl, ethyl, propyl, butyl, pentyl and hexyl; a branched chain lower alkyl selected from the group consisting of isopropyl, isobutyl, and t-butyl; a cyclic alkane selected from the group consisting of cyclopropyl, cyclobutyl, cyclohexyl, and cycloheptyl; a lower alkoxy in which the alkyl group is as mentioned above, n is 1 to 6; $R_3$ and $R_4$ are individually H, a lower straight or branched chain alkyl containing 1–15 carbon atoms as mentioned above; a cyclic alkane as defined above; an aryl residue selected from the group consisting of phenyl and naphthyl; an arylalkyl residue selected from the group consisting of benzyl and substituted benzyl, form a part of a heterocylic ring selected from the group consisting of pyrrolidine and piperidine, form a heterocyclic ring with additional heteroatoms O, N, S selected from the group consisting of piperazine, morpholine, oxazole, oxathiazole and oxathiazine; an alkoxy carbonyl alkane such as $R_6COOR_7$, wherein $R_6$ is $(CH_2)n$ (n=1–3) and $R_7$ is a lower alkyl as defined above, said process comprising steps of:

(a) reacting a substituted β-naphthol of formula II with a dihaloalkane of formula III in an organic solvent in the presence of a base to obtain an intermediate compound of formula IV,

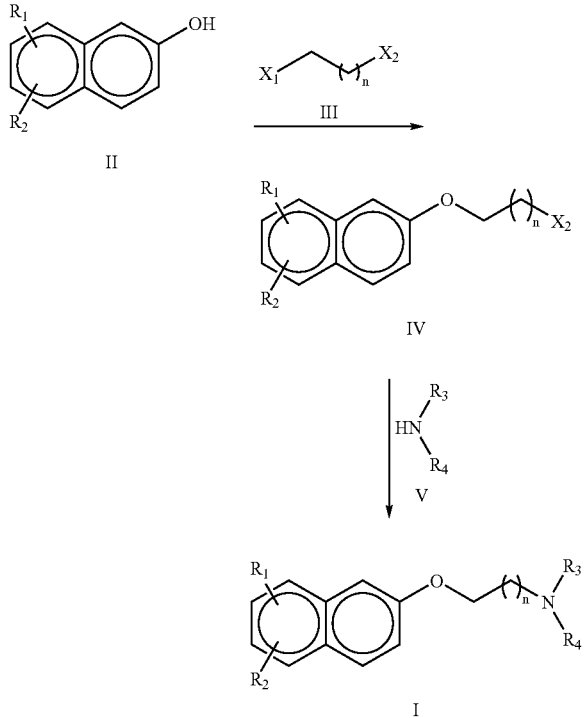

wherein $R_1$ and $R_2$ are defined as above and wherein $X_1$ and $X_2$ may be same or different halogens, and (b) reacting a compound of formula IV with an amine of formula V in the presence of an acid binding agent optionally in an organic solvent to obtain a compound of formula I, wherein $X_2$ is a halogen and $R_3$ and $R_4$ are defined as above.

25. The method as claimed in claim 24, wherein said ω-naphthyloxy amino alkane compound selected from the group consisting of:

(i) N-(4-Methoxyphenyl)-[3-(naphthalen-2-yloxy)propyl] amine [I: $R_1=R_2=R_3=H$, $R_4$=4-methoxyphenyl, n=3]

(ii) N-(4-Methoxyphenyl)-N-propyl[3-(naphthalen-2-yloxy)propyl] amine [I: $R_1=R_2=H$, $R_3$=propyl, $R_4$=4-methoxyphenyl, n=3]

(iii) N-(4-Methoxyphenyl)-[3-(naphthalen-2-yloxy)propyl]amino acetic acid ethyl ester [I: $R_1=R_2=H$, $R_3=CH_2COOEt$, $R_4$=4-methoxy phenyl, n=3]

(iv) N-Benzyl-[2-(naphthalen-2-yloxy)-ethyl] amine [I: $R_1=R_2=R_3=H$, $R_4$=benzyl, n=2]

(v) N-(4-Methoxyphenyl)-[2-(naphthalen-2-yloxy)ethyl] amine [I: $R_1=R_2=R_3=H$, $R_4$=4-methoxy phenyl, n=2]

(vi) N-(4-Methoxyphenyl)-[3-(naphthalen-2-yloxy)propyl] amine [I: $R_1=R_2=R_3=H$, $R_4$=4-methoxy phenyl, n=3]

(vii) N-(4-Methoxyphenyl)-[4-(naphthalen-2-yloxy)butylamine [I: $R_1=R_2=R_3=H$, $R_4$=4-methoxyphenyl, n=4]

(viii) N-(4-Methylphenyl)-[2-(naphthalen-2-yloxy)ethyl] amine [I: $R_1=R_2=R_3=H$, $R_4$=4-methyl phenyl, n=2]

(ix) N-(4-Methylphenyl)-[3-(naphthalen-2-yloxy)propyl] amine [I: $R_1=R_2=R_3=H$, $R_4$=4-methylphenyl, n=3]

(x) N-(4-Methylphenyl)-[4-(naphthalen-2-yloxy)butyl] amine [I: $R_1=R_2=R_3=H$, $R_4$=4-methyl phenyl, n=4]

(xi) N-(3-Methoxybenzyl)-[2-napthalen-2-yloxy)ethyl] amine [I: $R_1=R_2=R_3=H$, $R_4$=3-methoxy benzyl, n=2]

(xii) N-(3-Methoxybenzyl)-[3-napthalen-2-yloxy)propyl] amine [I: $R_1=R_2=R_3=H$, $R_4$=3-methoxy benzyl, n=3]

(xiii) N-(3-Methoxybenzyl)-[4-napthalen-2-yloxy)butyl] amine [I: $R_1=R_2=R_3=H$, $R_4$=3-methoxy benzyl, n=4]

(xiv) N-Benzyl-[2-(naphthalen-2-yloxy)-ethyl] amine [I: $R_1=R_2=R_3=H$, $R_4$=benzyl, n=2]

(xv) N-Benzyl-[3-(naphthalen-2-yloxy)-propyl] amine [I: $R_1=R_2=R_3=H$, $R_4$=benzyl, n=3]

(xvi) N-Benzyl-[4-(naphthalen-2-yloxy)-butyl] amine [I: $R_1=R_2=R_3=H$, $R_4$=benzyl, n=4]

(xvii) N-Cyclohexyl-[2-(naphthalen-2-yloxy)-ethyl] amine [I: $R_1=R_2=R_3=H$, $R_4$cyclohexyl, n=2]

(xviii) N-Cyclohexyl-[3-(naphthalen-2-yloxy)propyl] amine [I: $R_1=R_2=R_3=H$, $R_4$=cyclohexyl, n=3]

(xix) N-Cyclohexyl-[4-(naphthalen-2-yloxy)-butyl] amine [I: $R_1=R_2=R_3=H$, $R_4$=cyclohexyl, n=4]

(xx) N-(2-Ethyl-n-hexyl)-[2-(naphthalen-2-yloxy)ethyl] amine [I: $R_1=R_2=R_3=H$, $R_4$=2-ethyl n-hexyl, n=2]

(xxi) N-(2-Ethyl-n-hexyl)-[3-(naphthalen-2-yloxy)propyl] amine [I: $R_1=R_2=R_3=H$, $R_4$=2-ethyl-n-hexyl, n=3]

(xxii) N-(2-Ethyl-n-hexyl)-[4-(naphthalen-2-yloxy)butyl] amine [I: $R_1=R_2=R_3=H$, $R_4$=2-ethyl-n-hexyl, n=4]

(xxiii) N-(n-Dodecyl)-[2-(naphthalen-2-yloxy)-ethyl] amine [I: $R_1=R_2=R_3=H$, $R_4$=n-dodecyl, n=2]

(xxiv) N-(n-Dodecyl)-[3-(naphthalen-2-yloxy)-propyl] amine [I: $R_1=R_2=R_3=H$, $R_4$=n-dodecyl, n=3]

(xxv) N-(n-Dodecyl)-[4-(naphthalen-2-yloxy)-butyl] amine [I: $R_1=R_2=R_3=H$, $R_4$=n-dodecyl, n=4]

(xxvi) N-(Isoamyl)-[2-(naphthalen-2-yloxy)-ethyl] amine [I: $R_1=R_2=R_3=H$, $R_4$=isoamyl, n=2]

(xxvii) N-(Isoamyl)-[3-(naphthalen-2-yloxy)-propyl] amine [I: $R_1=R_2=R_3=H$, $R_4$=isoamyl, n=3]

(xxviii) N-(Isoamyl)-[4-(naphthalen-2-yloxy)-butyl] amine [I: $R_1=R_2=R_3=H$, $R_4$=isoamyl, n=4]

(xxix) N-(3-Phenylpropyl)-[2-(naphthalen-2-yloxy)ethyl] amine [I: $R_1=R_2=R_3=H$, $R_4$=2-phenyl ethyl, n=2]

(xxx) N-(3-Phenylpropyl)-[3-(naphthalen-2-yloxy)propyl] amine [I: $R_1=R_2=R_3=H$, $R_4$=2-phenylethyl, n=3]

(xxxi) N-(3-Phenylpropyl)-[4-(naphthalen-2-yloxy)butyl] amine [I: $R_1=R_2=R_3=H$, $R_4$=2-phenylethyl, n=4]

(xxxii) N-(n-Octyl)-[2-(naphthalen-2-yloxy)ethyl] amine [I: $R_1=R_2=R_3=H$, $R_4$=n-octyl, n=2]

(xxxiii) N-(n-Octyl)-[3-(naphthalen-2-yloxy)propyl] amine [I: $R_1=R_2=R_3=H$, $R_4$=n-octyl, n=3]

(xxxiv) N-(n-Octyl)-[3-(napthalen-2-yloxy)butyl] amine [I: $R_1=R_2=R_3=H$, $R_4$=n-octyl, n=4]

(xxxv) N-(n-Butyl)-[4-(naphthalen-2-yloxy)butyl] amine [I: $R_1=R_2=R_3=H$, $R_4$=n-butyl, n=4]

(xxxvi) N-(n-Propyl)-[4-(naphthalen-2-yloxy)butyl] amine [I: $R_1$50 $R_2=R_3=H$, $R_4$=n-propyl, n=4]

(xxxvii) N-(2-Phenylethyl)-[2-(naphthalen-2-yloxy)butyl] amine [I: $R_1=R_2=R_3=H$, $R_4=$2-phenyl-ethyl, n=4]

(xxxviii) N-(Piperidinyl)-[4-(naphthalen-2-yloxy)butyl] amine [I: $R_1=R_2=R_3=H$, $R_4=$Piperidinyl, n=4]

(xxxix) N-(n-Butyl)-[3-(naphthalen-2-yloxy)propyl] amine [I: $R_1=R_2=R_3=H$, $R_4=$n-butyl, n=3]

(xl) N-(n-Propyl)-[3-(naphthalen-2-yloxy)propyl] amine [I: $R_1=R_2=R_3=H$, $R_4=$n-propyl, n=3]

(xli) N-(2-Phenylethyl)-[3-(naphthalen-2-yloxy)propyl] amine [I: $R_1=R_2=R_3=H$, $R_4=$2-phenylethyl, n=3]

(xlii) N-(Piperidinyl)-[3-(naphthalen-2-yloxy)propyl] amine [I: $R_1=R_2=R_3=H$, $R_4=$Piperidinyl, n=3]

(xliii) N-(4-Methoxyphenyl)-N-methyl[3-(naphthalen-2-yloxy)propyl] amine [I: $R_1=R_2=H$, $R_3=$methyl, $R_4=$4-methoxyphenyl, n=3]

(xliv) N-(4 Methoxyphenyl)-N-ethyl[3-(naphthalen-2-yloxy)propyl] amine [I: $R_1=R_2=H$, $R_3=$ethyl, $R_4=$4-methoxyphenyl, n=3]

(xlv) N-(4-Methoxyphenyl)-N-propyl[3-(naphthalen-2-yloxy)propyl] amine [I: $R_1=R_2=H$, $R_3=$propyl, $R_4=$4-methoxyphenyl, n=3]

(xlvi) N-(4-Methoxyphenyl)-N-butyl[3-(naphthalen-2-yloxy)propyl] amine [I: $R_1=R_2=H$, $R_3=$n-butyl, $R_4=$4-methoxyphenyl, n=3]

(xlvii) N-(4-Methoxyphenyl)-[3-(naphthalen-2-yloxy)propyl]amino } acetic acid ethyl ester [I: $R_1=R_2=H$, $R_3=-CH_2COOEt$, $R_4=$4-methoxyphenyl, n=3]

(xlviii) 2,7-Bis[3-(4methoxyphenylamino)propyloxy] naphthalene[ I: $R_1=$4-methoxyphenyl amino propyloxy, $R_2$ & $R_3=H$, $R_4=$4-methoxyphenyl] and (xlix) 2,6-Bis[3-(4-methoxyphenylamino)propyloxy] naphthalene [I: $R_2=$4-methoxyphenyl amino propyloxy, $R_1$ & $R_3=H$, $R_4=$4-methoxyphenyl].

26. The method as claimed in claim 24, wherein the organic solvents in step (a) are selected from group comprising of dry acetone, ethanol, methanol, dimethyl sulphoxide (DMSO), dimethylformamide (DMF), hexamethylphosphoric triamide (HMPA) and acetonitrile.

27. The method as claimed in claim 24, wherein the base in step (a) is selected from the group comprising of cesium carbonate, potassium carbonate, sodium carbonate lithium carbonate.

28. The method as claimed in claim 24, wherein the organic solvents in step (b) are selected from group comprising of dimethyl sulphoxide (DMSO), dimethylformamide (DMF), hexamethylphosphoric triamide (HMPA) or acetonitrile.

29. The method as claimed in claim 24, wherein the temperature in step (a) is in range of about 50° C. to 100° C.

30. The method as claimed in claim 29, wherein the temperature is preferably in the range of about 60° C. to 80° C.

31. The method as claimed in claim 24, wherein the temperature in step (b) in the range of about 120° C. to 180° C.

32. The method as claimed in claim 31, wherein the temperature is preferably in the range of about 130° C. to 150° C.

33. The method as claimed in claim 24, wherein the reaction time in steps (a) and (b) is in the range of about 4 hours to 13 hours.

34. The method as claimed in claim 33, wherein the reaction time in steps (a) and (b) is in the range of about 5 hours to 12 hours.

35. The method as claimed in claim 24, wherein the 107-naphthyloxy amino alkane compound of formula 1 has a melting point in the range of about 75° C. to 170° C.

36. The method as claimed in claim 35, wherein the 107-naphthyloxy amino alkane compound of formula 1 has a melting point in the range of about 78° C. to 160° C.

37. The method as claimed in claim 24, wherein the purity of said 107-naphthyloxy amino alkane compound of formula I is in the range of about 80% to 100%.

38. The method as claimed in claim 24, wherein the dosage of the said 107-naphthyloxy amino alkane compound is in the range of about 250–350 µmol/Kg.

39. The method as claimed in claim 38, wherein the dosage of the said 107-naphthyloxy amino alkane compound is about 300 µmol/Kg.

40. The method as claimed in claim 24, wherein the said 107-naphthyloxy amino alkane compound is administered in form of a syrup, a capsule, a tablet, a suspension or an intravenous preparation.

41. The method as claimed in claim 40, wherein the 107-naphthyloxy amino alkane compound is administered orally, intranasally, or parenterally.

42. The method as claimed in claim 24, wherein said 107-naphthyloxy amino alkane compound lower the plasma concentration of cholesterol by about 30%.

43. The method as claimed in claim 42, wherein said 107-naphthyloxy amino alkane compound lowers the plasma concentration of cholesterol preferably by about 26%.

44. The method as claimed in claim 24, wherein said 107-naphthyloxy amino alkane compound lowers the plasma concentration of phospholipids by about 35%.

45. The method as claimed in claim 44, wherein said 107-naphthyloxy amino alkane compound lowers the plamsa concentration of phospholipids preferably by about 30%.

46. The method as claimed in claim 24, wherein said 107-naphthyloxy amino alkane compound lowers the plasma concentration of triglycerides by about 50%.

47. The method as claimed in claim 46, wherein said 107-naphthyloxy amino alkane compound lowers the plasma concentration of triglycerides preferably by about 48%.

48. The method as claimed in claim 24, wherein said 107-naphthyloxy amino alkane compound enhances the plasma concentration of high-density lipoproteins (HDL) by about 20%.

49. The method as claimed in claim 48, wherein said 107-naphthyloxy amino alkane compound enhances the plasma concentration of high-density lipoproteins by about 15%.

50. The method as claimed in claim 24, wherein said 107-naphthyloxy amino alkane compound lowers the plasma glucose (GLU) concentration by about 40%.

51. The method as claimed in claim 50, wherein said 107-naphthyloxy amino alkane compound lowers the plasma glucose (GLU) concentration preferably by about 30%.

52. The method as claimed in claim 24 wherein said 107-naphthyloxy amino alkane compound lowers the plasma glycerol (GLY) concentration by about 20%.

53. The method as claimed in claim 52 wherein, the dosage of the 107-naphthyloxy amino alkane compound lowers the plasma glycerol concentration by about 14%.

54. The method as claimed in claim 24, wherein said 107-naphthyloxy amino alkane compound lowers the plasma glucose concentration in about 30 min to 10 hours during post drug administration.

55. The method as claimed in claim 54, wherein said 107-naphthyloxy amino alkane compound lowers the plasma glucose concentration in about 1 hr to 7 hrs during post drug administration.

56. A pharmaceutical composition for the treatment of cardiovascular disorders (CVS) and of hyperglycemic condition (diabetes) in mammals, including humans, said composition comprising as the active ingredient, a therapeutically effective dosage of an ω-naphthyloxy amino alkane compound having structural formula I,

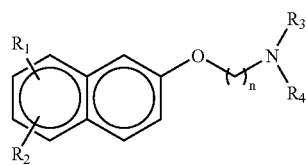

wherein, $R_1$ and $R_2$ are individually H, a lower alkyl containing 1–6 carbon atoms selected from the group consisting of methyl, ethyl, propyl, butyl, pentyl, and hexyl; a branched chain lower alkyl selected from the group consisting of isopropyl, isobutyl, and t-butyl; a cyclic alkane selected from the group consisting of cyclopropyl, cyclobutyl, cyclohexyl and cycloheptyl; a lower alkoxy in which the alkyl group is as mentioned above, n is 1 to 6; $R_3$ and $R_4$ are individually H, a lower straight or branched chain alkyl containing 1–15 carbon atoms as mentioned above; a cyclic alkane as defined above; an aryl residue selected from the group consisting of phenyl and naphthyl; an arylalkyl residue selected from the group consisting of benzyl and substituted benzyl, form a part of a heterocyclic ring selected from the group consisting of pyrrolidine and piperidine, form a heterocyclic ring with additional heteroatoms O, N, S selected from the group consisting of piperazine, morpholine, oxazole, oxathiazole and oxathiazine; an alkoxy carbonyl alkane represented by the formula $R_6COOR_7$, wherein $R_6$ is $(CH_2)n$ (n=1–3) and $R_7$ is a lower alkyl as defined above, optionally along with acceptable salt/s, carrier/s or diluent/s wherein the salts/carries/diluents are selected from the group consisting of lactose, sodium chloride, potassium chloride, magnesium sulphate, potassium phosphate, magnesium succinate, sodium carbonate, sodium sulfate, potassium acid phosphate and calcium bicarbonate.

57. The composition as claimed in claim 56, wherein said ω-naphthyloxy amino alkane compound is selected from the group consisting of:

(i) N-(4-Methoxyphenyl)-[3-(naphthalen-2-yloxy)propyl] amine [I: $R_1=R_2=R_3=H$, $R_4$=4-methoxyphenyl, n=3]

(ii) N-(4-Methoxyphenyl)-N-propyl[3-(naphthalen-2-yloxy)propyl] amine [I: $R_1=R_2=H$, $R_3$=propyl $R_4$=4-methoxyphenyl, n=3]

(iii) N-(4-Methoxyphenyl)-[3-(naphthalen-2-yloxy)propyl] amino acetic acid ethyl ester [I: $R_1=R_2=H$, $R_3=CH_2COOEt$, $R_4$=4-methoxy phenyl, n-3]

(iv) N-Benzyl-[2-(naphthalen-2-yloxy)-ethyl] amine [I: $R_1=R_2=R_3=H$, $R_4$=benzyl, n=2]

(v) N-(4-Methoxyphenyl)-[2-(naphthalen-2-yloxy)ethyl] amine [I: $R_1=R_2=R_3=H$, $R_4$=4-methoxy phenyl, n=2]

(vi) N-(4-Methoxyphenyl)-[3-(naphthalen-2-yloxy)propyl] amine [I: $R_1=R_2=R_3=H$, $R_4$=4-methoxyphenyl, n=3]

(vii) N-(4-Methoxyphenyl)-[4-(naphthalen-2-yloxy)butylamine [I: $R_1=R_2=R_3=H$, $R_4$=4-methoxyphenyl, n=4]

(viii) N-(4-Methylphenyl)-[2-(naphthalen-2-yloxy)ethyl] amine [I: $R_1=R_2=R_3=H$, $R_4$=4-methyl phenyl, n=2]

(ix) N-(4-Methylphenyl)-[3-(naphthalen-2-yloxy)propyl] amine [I: $R_1=R_2=R_3=H$, $R_4$=4-methylphenyl, n-3]

(x) N-(4-Methylphenyl)-[4-(naphthalen-2-yloxy)butyl] amine [I: $R_1=R_2=R_3=H$, $R_4$=4-methyl phenyl, n-4]

(xi) N-(3-Methoxybenzyl)-[2-napthalen-2-yloxy)ethyl] amine [I: $R_1=R_2=R_3=H$, $R_4$=3-methoxybenzyl, n=2]

(xii) N-(3-Methoxybenzyl)-[3-napthalen-2-yloxy)propyl] amine [I: $R_1=R_2=R_3=H$, $R_4$=3-methoxy benzyl, n=3]

(xiii) N-(3-Methoxybenzyl)-[4-napthalen-2-yloxy)butyl] amine [I: $R_1=R_2=R_3=H$, $R_4$=3-methoxybenzyl, n=4]

(xiv) N-Benzyl-[2-(naphthalen-2-yloxy)-ethyl] amine [I: $R_1=R_2=R_3=H$, $R_4$=benzyl, n=2]

(xv) N-Benzyl-[3-(naphthalen-2-yloxy)-propyl] amine [I: $R_1=R_2=R_3=H$, $R_4$=benzyl, n=3]

(xvi) N-Benzyl-[4-(naphthalen-2-yloxy)-butyl] amine [I: $R_1=R_2=R_3=H$, $R_4$=benzyl, n=4]

(xvii) N-Cyclohexyl-[2-(naphthalen-2-yloxy)-ethyl] amine [I: $R_1=R_2=R_3=H$, $R_4$=cyclohexyl, n=2]

(xviii) N-Cyclohexyl-[3-(napthalen-2-yloxy)propyl] amine [I: $R_1=R_2=R_3=H$, $R_4$=cyclohexyl, n=3]

(xix) N-Cyclohexyl-[4-(naphthalen-2-yloxy)-butyl] amine [I: $R_1=R_2=R_3=H$, $R_4$=cyclohexyl, n=4]

(xx) N-(2-Ethyl-n-hexyl)-[2-(naphthalen-2-yloxy)ethyl] amine [I: $R_1=R_2=R_3=H$, $R_4$=2-ethyl n-hexyl, n=2]

(xxi) N-(2-Ethyl-n-hexyl)-[3-(naphthalen-2-yloxy)propyl] amine [I: $R_1=R_2=R_3=H$, $R_4$=2-ethyl-n-hexyl, n=3]

(xxii) N-(2-Ethyl-n-hexyl)-[4-(naphthalen-2-yloxy)butyl] amine [I: $R_1=R_2=R_3=H$, $R_4$=2-ethyl-n-hexyl, n=4]

(xxiii) N-(n-Dodecyl)-[2-(naphthalen-2-yloxy)-ethyl] amine [I: $R_1=R_2=R_3=H$, $R_4$=n-dodecyl, n=2]

(xxiv) N-(n-Dodecyl)-[3-(naphthalen-2-yloxy)-propyl] amine [I: $R_1=R_2=R_3=H$, $R_4$=n-dodecyl, n=3]

(xxv) N-(n-Dodecyl)-[4-(naphthalen-2-yloxy)-butyl] amine [I: $R_1=R_2=R_3=H$, $R_4$=n-dodecyl, n=4]

(xxvi) N-(Isoamyl)-[2-(naphthalen-2-yloxy)-ethyl] amine [I: $R_1=R_2=R_3=H$, $R_4$=isoamyl, n=2]

(xxvii) N-(Isoamyl)-[3-(naphthalen-2-yloxy)-propyl] amine [I: $R_1=R_2=R_3=H$ $R_4$=isoamyl, n=3]

(xxviii) N-(Isoamyl)-[4-(naphthalen-2-yloxy)-butyl] amine [I: $R_1=R_2=R_3=H$, $R_4$=isoamyl, n=4]

(xxix) N-(3-Phenylpropyl)-[2-(naphthalen-2-yloxy)ethyl] amine [I: $R_1=R_2=R_3=H$, $R_4$=2-phenylethyl, n=2]

(xxx) N-(3-Phenylpropyl)-[3-(naphthalen-2-yloxy)propyl] amine [I: $R_1=R_2=R_3=H$, $R_4$=2-phenylethyl, n=3]

(xxxi) N-(3-Phenylpropyl)-[4-(naphthalen-2-yloxy)butyl] amine [I: $R_1=R_2=R_3=H$, $R_4$=2-phenylethyl, n=4]

(xxxii) N-(n-Octyl)-[2-(naphthalen-2-yloxy)ethyl] amine [I: $R_1=R_2=R_3=H$, $R_4$=n-octyl, n=2]

(xxxiii) N-(n-Octyl)-[3-(naphthalen-2-yloxy)propyl] amine [I: $R_1=R_2=R_3=H$, $R_4$=n-octyl, n=3]

(xxxiv) N-(n-Octyl)-[3-(napthalen-2-yloxy)butyl] amine [I: $R_1=R_2=R_3=H$, $R_4$=n-octyl, n=4]

(xxxv) N-(n-Butyl)-[4-(naphthalen-2-yloxy)butyl] amine [I: $R_1=R_2=R_3=H$, $R_4$=n-butyl, n=4]

(xxxvi) N-(n-Propyl)-[4-(naphthalen-2-yloxy)butyl] amine [I: $R_1=R_2=R_3=H$, $R_4$=n-propyl, n=4]

(xxxvii) N-(2-Phenylethyl)-[2-(naphthalen-2-yloxy)butyl] amine [I: $R_1=R_2=R_3=H$, $R_4=$2-phenyl-ethyl, n=4]

(xxxviii) N-(Piperidinyl)-[4-(naphthalen-2-yloxy)butyl] amine [I: $R_1=R_2=R_3=H$, $R_4=$Piperidinyl, n=4]

(xxxix) N-(n-Butyl)-[3-(naphthalen-2-yloxy)propyl] amine [I: $R_1=R_2=R_3=H$, $R_4=$n-butyl, n=3]

(xl) N-(n-Propyl)-[3-(naphthalen-2-yloxy)propyl] amine [I: $R_1=R_2=R_3=H$, $R_4=$n-propyl, n=3]

(xli) N-(2-Phenylethyl)-[3-(naphthalen-2-yloxy)propyl] amine [I: $R_1=R_2=R_3=H$, $R_4=$2-phenyl ethyl, n=3]

(xlii) N-(Piperidinyl)-[3-(naphthalen-2-yloxy)propyl] amine [I: $R_1=R_2=R_3=H$, $R_4=$Piperidinyl, n=3]

(xliii) N-(4-Methoxyphenyl)-N-methyl[3-(naphthalen-2-yloxy)propyl] amine [I: $R_1=R_2=H$, $R_3=$methyl, $R_4=$4-methoxyphenyl, n=3]

(xliv) N-(4 Methoxyphenyl)-N-ethyl[3-(naphthalen-2-yloxy)propyl] amine [I: $R_1=R_2=H$, $R_3=$ethyl, $R_4=$4-methoxyphenyl, n=3]

(xlv) N-(4-Methoxyphenyl)-N-propyl[3-(naphthalen-2-yloxy)propyl] amine [I: $R_1=R_2=H$, $R_3=$propyl, $R_4=$4-methoxyphenyl, n=3]

(xlvi) N-(4-Methoxyphenyl)-N-butyl[3-(naphthalen-2-yloxy)propyl] amine [I: $R_1=R_2=H$, $R_3=$n-butyl, $R_4=$4-methoxyphenyl, n=3]

(xlvii) N-(4-Methoxyphenyl)-[3-(naphthalen-2-yloxy) propyl amino acetic acid ethyl ester [I: $R_1=R_2=H$, $R_3=$—$CH_2COOEt$, $R_4=$4-methoxyphenyl, n=3]

(xlviii) 2,7-Bis[3-(4methoxyphenylamino)propyloxy] naphthalene [I: $R_1=$4-methoxyphenyl amino propyloxy, $R_2$ & $R_3=H$, $R_4=$4-methoxyphenyl] and (xlix) 2,6-Bis[3-(4-methoxyphenylamino)propyloxy] naphthalene [I: $R_2=$4-methoxyphenyl amino propyloxy, $R_1$ & $R_3=H$, $R_4=$4-methoxyphenyl].

58. The composition as claimed in claim 56, wherein the dosage of the said ω-naphthyloxy amino alkane compound is in the range of about 250–350 µmol/Kg.

59. The composition as claimed in claim 58, wherein the dosage of the said ω-naphthyloxy amino alkane compound is about 300 µmol/Kg.

60. The composition as claimed in claim 56, in the form of a syrup, a capsule, a tablet, a suspension or intravenous preparation.

61. The composition as claimed in claim 56, wherein the method of administration is oral, nasal, or parenteral.

62. The composition as claimed in claim 56, wherein said ω-naphthyloxy amino alkane compound lowers plasma concentration of cholesterol by about 30%.

63. The composition as claimed in claim 62, wherein said ω-naphthyloxy amino alkane compound lowers plasma concentration of cholesterol by about 26%.

64. The composition as claimed in claim 56, wherein said ω-naphthyloxy amino alkane compound lowers plasma concentration of phospholipids by about 35%.

65. The composition as claimed in claim 64, wherein said ω-naphthyloxy amino alkane compound lowers plasma concentration of phospholipids by about 30%.

66. The composition as claimed in claim 56, wherein said ω-naphthyloxy amino alkane compound lowers plasma concentration of triglycerides by about 50%.

67. The composition as claimed in claim 66, wherein said ω-naphthyloxy amino alkane compound lowers plasma concentration of triglycerides by about 48%.

68. The composition as claimed in claim 56, wherein said ω-naphthyloxy amino alkane compound enhances plasma concentration of high-density lipoprotein (HDL) by about 20%.

69. The composition as claimed in claim 68, wherein said ω-naphthyloxy amino alkane compound enhances plasma concentration of high-density lipoprotein (HDL) by about 15%.

70. The composition as claimed in claim 56, wherein said ω-naphthyloxy amino alkane compound lowers palsma glucose (GLU) concentration by about 40%.

71. The composition as claimed in claim 70, wherein said ω-naphthyloxy amino alkane compound lowers plasma glucose (GLU) concentration by about 30%.

72. The composition as claimed in claim 56, wherein, said ω-naphthyloxy amino alkane compound lowers plasma glycerol (GLY) concentration by about 20%.

73. The composition as claimed in claim 72, wherein said ω-naphthyloxy amino alkane compound lowers plasma glycerol concentration by about 14%.

74. The composition as claimed in claim 56 wherein said ω-naphthyloxy amino alkane compound lower plasma glucose concentration in about 30 min to 10 hours post administration.

75. The composition as claimed in claim 74 wherein said ω-naphthyloxy amino alkane compound lowers plasma glucose concentration in about 1 hr to 7 hrs post administration.

76. The method for treatment of cardiovascular disorders and hyperglycemia (diabetes) comprising administering a composition comprising as an active ingredient, a therepeutically effective dosage of a ω-naphthyloxy amino alkane compound having structural formula I,

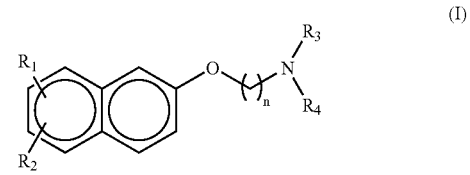

wherein $R_1$ and $R_2$ are individually H, a lower alkyl containing 1–6 carbon atoms, selected from the group consisting of methyl, ethyl, propyl, butyl, pentyl and hexyl; a branched chain lower alkyl selected from the group consisting of isopropyl, isobutyl and t-butyl; a cyclic alkane selected from the group consisting of cyclopropyl, cyclobutyl, cyclohexyl and cycloheptyl; a lower alkoxy in which the alkyl group is as mentioned above, n is 1 to 6; $R_3$ and $R_4$ are individually H, a lower straight or branched chain alkyl containing 1–15 carbon atoms as mentioned above; a cyclic alkane as defined above; an aryl residue selected from the group consisting of phenyl and naphthyl; an arylalkyl residue selected from the group consisting of benzyl, substituted benzyl, form a part of a heterocyclic ring selected from the group consisting of pyrrolidine and piperidine, form a heterocyclic ring with additional heteroatoms O, N, S selected from the group consisting of piperazine, morpholine, oxazole, oxathiazole and oxathiazine; an alkoxy carbonyl alkane represented by the formula $R_6COOR_7$, wherein $R_6$ is $(CH_2)n$ (n=1–3) and $R_7$ is a lower alkyl as defined above, and acceptable salt/s, carrier/s or diluent/s, wherein the salts/carriers/diluents are selected from the group consisting of lactose, sodium chloride, potassium chloride, magnesium sulphate, magnesium chloride, potassium sulfate, sodium sulfate, lithium sulphate, sodium phosphate, potasssium phosphate, magnesium succinate, sodium carbonate, sodium sulfate, potassium acid phosphate and calcium bicarbonate.

77. A method as claimed in claim 76 wherein said ω-naphthyloxy amino alkane compound is selected from the group consisting of:

(i) N-(4-Methoxyphenyl)-[3-(naphthalen-2-yloxy)propyl] amine [I: $R_1=R_2=R_3=H$, $R_4=$4-methoxyphenyl, n=3]

(ii) N-(4-Methoxyphenyl)-N-propyl[3-(naphthalen-2-yloxy)propyl] amine [I: $R_1=R_2=H$, $R_3=$propyl $R_4=$4-methoxyphenyl, n=3]

(iii) N-(4-Methoxyphenyl)-[3-(naphthalen-2-yloxy)propyl] amino acetic acid ethyl ester [I: $R_1=R_2=H$, $R_3=CH_2COOEt$, $R_4=$4-methoxy phenyl, n=3]

(iv) N-Benzyl-[2-(naphthalen-2-yloxy)-ethyl] amine [I: $R_1=R_2=R_3=H$, $R_4=$benzyl, n=2]

(v) N-(4-Methoxyphenyl)-[2-(naphthalen-2-yloxy)ethyl] amine [I: $R_1=R_2=R_3=H$, $R_4=$4-methoxyphenyl, n=2]

(vi) N-(4-Methoxyphenyl)-[3-(naphthalen-2-yloxy)propyl] amine [I: $R_1=R_2=R_3=H$, $R_4=$4-methoxyphenyl, n=3]

(vii) N-(4-Methoxyphenyl)-[4-(naphthalen-2-yloxy)butylamine [I: $R_1=R_2=R_3=H$, $R_4=$4-methoxyphenyl, n=4]

(viii) N-(4-Methylphenyl)-[2-(naphthalen-2-yloxy)ethyl] amine [I: $R_1=R_2=R_3=H$, $R_4=$4-methyl phenyl, n=2]

(ix) N-(4-Methylphenyl)-[3-(naphthalen-2-yloxy)propyl] amine [I: $R_1=R_2=R_3=H$, $R_4=$4-methylphenyl, n=3]

(x) N-(4-Methylphenyl)-[4-(naphthalen-2-yloxy)butyl] amine [I: $R_1=R_2=R_3=H$, $R_4=$4-methyl phenyl, n=4]

(xi) N-(3-Methoxybenzyl)-[2-napthalen-2-yloxy)ethyl] amine [I: $R_1=R_2=R_3=H$, $R_4=$3-methoxy benzyl, n=2]

(xii) N-(3-Methoxybenzyl)-[3-napthalen-2-yloxy)propyl] amine [I: $R_1=R_2=R_3=H$, $R_4=$3-methoxy benzyl, n=3]

(xiii) N-(3-Methoxybenzyl)-[4-napthalen-2-yloxy)butyl] amine [I: $R_1=R_2=R_3=H$, $R_4=$3-methoxybenzyl, n=4]

(xiv) N-Benzyl-[2-(naphthalen-2-yloxy)-ethyl]aamine [I: $R_1=R_2=R_3=H$, $R_4=$benzyl, n=2]

(xv) N-Benzyl-[3-(naphthalen-2-yloxy)-propyl] amine [I: $R_1=R_2=R_3=H$, $R_4=$benzyl, n=3]

(xvi) N-Benzyl-[4-(naphthalen-2-yloxy)-butyl] amine [I: $R_1=R_2=R_3=H$, $R_4=$benzyl, n=4]

(xvii) N-Cyclohexyl-[2-(naphthalen-2-yloxy)-ethyl] amine [I: $R_1=R_2=R_3=H$, $R_4=$cyclohexyl, n=2]

(xviii) N-Cyclohexyl-[3-(naphthalen-2-yloxy)propyl] amine [I: $R_1=R_2=R_3=H$, $R_4=$cyclohexyl, n=3]

(xix) N-Cyclohexyl-[4-(naphthalen-2-yloxy)-butyl] amine [I: $R_1=R_2=R_3=H$, $R_4=$cyclohexyl, n=4]

(xx) N-(2-Ethyl-n-hexyl)-[2-(naphthalen-2-yloxy)ethyl] amine [I: $R_1=R_2=R_3=H$, $R_4=$2-ethyl n-hexyl, n=2]

(xxi) N-(2-Ethyl-n-hexyl)-[3-(naphthalen-2-yloxy)propyl] amine [I: $R_1=R_2=R_3=H$, $R_4=$2-ethyl-n-hexyl, n=3]

(xxii) N-(2-Ethyl-n-hexyl)-[4-(naphthalen-2-yloxy)butyl] amine [I: $R_1=R_2=R_3=H$, $R_4=$2-ethyl-n-hexyl, n=4]

(xxiii) N-(n-Dodecyl)-[2-(naphthalen-2-yloxy)-ethyl] amine [I: $R_1=R_2=R_3=H$, $R_4=$n-dodecyl, n=2]

(xxiv) N-(n-Dodecyl)-[3-(naphthalen-2-yloxy)-propyl] amine [I: $R_1=R_2=R_3=H$, $R_4=$n-dodecyl, n=3]

(xxv) N-(n-Dodecyl)-[4-(naphthalen-2-yloxy)-butyl] amine [I: $R_1=R_2=R_3=H$, $R_4=$n-dodecyl, n=4]

(xxvi) N-(Isoamyl)-[2-(naphthalen-2-yloxy)-ethyl] amine [I: $R_1=R_2=R_3=H$, $R_4=$isoamyl, n=2]

(xxvii) N-(Isoamyl)-[3-(naphthalen-2-yloxy)-propyl] amine [I: $R_1=R_2=R_3=H$, $R_4=$isoamyl, n=3]

(xxviii) N-(Isoamyl)-[4-(naphthalen-2-yloxy)-butyl] amine [I: $R_1=R_2=R_3=H$, $R_4=$isoamyl, n=4]

(xxix) N-(3-Phenylpropyl)-[2-(naphthalen-2-yloxy)ethyl] amine [I: $R_1=R_2=R_3=H$, $R_4=$2-phenyl ethyl, n=2]

(xxx) N-(3-Phenylpropyl)-[3-(naphthalen-2-yloxy)propyl] amine [I: $R_1=R_2=R_3=H$, $R_4=$2-phenylethyl, n=3]

(xxxi) N-(3-Phenylpropyl)-[4-(naphthalen-2-yloxy)butyl] amine [I: $R_1=R_2=R_3=H$, $R_4=$2-phenylethyl, n=4]

(xxxii) N-(n-Octyl)-[2-(naphthalen-2-yloxy)ethyl] amine [I: $R_1=R_2=R_3=H$, $R_4=$n-octyl, n=2]

(xxxiii) N-(n-Octyl)-[3-(naphthalen-2-yloxy)propyl] amine [I: $R_1=R_2=R_3=H$, $R_4=$n-octyl, n=3]

(xxxiv) N-(n-Octyl)-[3-(napthalen-2-yloxy)butyl] amine [I: $R_1=R_2=R_3=H$, $R_4=$n-octyl, n=4]

(xxxv) N-(n-Butyl)-[4-(naphthalen-2-yloxy)butyl] amine [I: $R_1=R_2=R_3=H$, $R_4=$n-butyl, n=4]

(xxxxvi) N-(n-Propyl)-[4-(naphthalen-2yloxy)butyl] amine [I: $R_1=R_2=R_3=H$, $R_4=$n-propyl, n=4]

(xxxvii) N-(2-Phenylethyl)-[2-(naphthalen-2-yloxy)butyl] amine [I: $R_1=R_2=R_3=H$, $R_4=$2-phenyl-ethyl, n=4]

(xxxviii) N-(Piperidinyl)-[4-napthalen-2-yloxy)butyl] amine [I: $R_1=R_2=R_3=H$, $R_4=$Piperidinyl, n=4]

(xxxix) N-(n-butyl)-[3-(napthalen-2-yloxy)propyl] amine [I: $R_1=R_2=R_3=H$, $R_4=$n-butyl, n=3]

(xl) N-(n-Propyl)-[3-(naphthalen-2-yloxy)propyl] amine [I: $R_1=R_2=R_3=H$, $R_4=$n-propyl, n=3]

(xli) N-(2-Phenylethyl)-[3-(naphthalen-2-yloxy)propyl] amine [I: $R_1=R_2=R_3=H$, $R_4=$2-phenylethyl, n=3]

(xlii) N-(Piperidinyl)-[3-(napthalen-2-yloxy)propyl] amine [I: $R_1=R_2=R_3=H$, $R_4=$piperidinyl, n=3]

(xliii) N-(4-Methoxyphenyl)-N-methyl[3-(naphthalen-2-yloxy)propyl] amine [I: $R_1=R_2=H$, $R_3=$methyl, $R_4=$4-methoxyphenyl, n=3]

(xliv) N-(4 Methoxyphenyl)-N-ethyl[3-(naphthalen-2-yloxy) propyl] amine [I: $R_1=R_2=H$, $R_3=$ethyl, $R_4=$4-methoxyphenyl, n=3]

(xlv) N-(4-Methoxyphenyl)-N-propyl[3-(naphthalen-2-yloxy)propyl] amine [I: $R_1=R_2=H$, $R_3=$propyl, $R_4=$4-methoxyphenyl, n=3]

(xlvi) N-(4-Methoxyphenyl)-N-butyl[3-(naphthalen-2-yloxy)propyl] amine [I: $R_1=R_2=H$, $R_3=$n-butyl, $R_4=$4-methoxyphenyl, n=3]

(xlvii) N-(4-Methoxyphenyl)-[3-(naphthalen-2-yloxy) propyl] amino acetic acid ethyl ester[I: $R_1=R_2=H$, $R_3=$—$CH_2COOEt$, $R_4=$4-methoxyphenyl, n=3]

(xlviii) 2,7-Bis[3-(4methoxyphenylamino)propyloxy] naphthalene [I: $R_1=$4-methoxyphenyl amino propyloxy, $R_2$ & $R_3=$H, $R_4=$4-methoxyphenyl] and (xlix) 2,6-Bis[3-(4-methoxyphenylamino)propyloxy] naphthalene[I: $R_2=$4-methoxyphenyl amino propyloxy, $R_1$ & $R_3=$H, $R_4=$4-methoxyphenyl].

78. The method as claimed in claim 76, wherein the dosage of the ω-naphthyloxy amino alkane compound is in the the range of about 250–350 μmol/Kg.

79. The method as claimed in claim 78, wherein the dosage of the ω-naphthyloxy amino alkane compound is about 300 μmol/Kg.

80. The method as claimed in claim 76, wherein the composition is administered in form of a syrup, a capsule, a tablet, a suspension or intravenously.

81. The method as claimed in claim 76, wherein the method of administration of said composition is oral, nasal, or parenteral.

82. The method as claimed in claim 76, wherein plasma cholesterol concentretion is lowered by about 30%.

83. The method as claimed in claim 82, wherein plasma cholesterol concentration is lowered by about 26%.

84. The method as claimed in claim 76, wherein plasma phospholipid concentration is lowered by about 35%.

85. The method as claimed in claim 84, wherein plasma phospholipid concentration is lowered by about 30%.

86. The method as claimed in claim 76, wherein plasma triglyceride concentration is lowered by about 50%.

87. The method as claimed in claim 86, wherein plasma triglyceride concentration is lowered by about 48%.

88. The method as claimed in claim 76, wherein plasma high-density lipoprotein (HDL) concentration is enhanced by about 20%.

89. The method as claimed in claim 88, wherein plasma high-density lipoprotein (HDL) concentration is enhanced by about 15%.

90. The method as claimed in claim 76, wherein plasma glucose (GLU) concentration is lowered by about 40%.

91. The method as claimed in claim 90, wherein plasma glucose (GLU) concentration is lowered by about 30%.

92. The method as claimed in claim 76 wherein plasma glycerol (GLY) concentration is lowered by about 20%.

93. The method as claimed in claim 92 wherein plasma glycerol concentration is lowered by about 14%.

94. The method as claimed in claim 76, wherein plasma glucose concentration is lowered in about 30 min to 10 hours post administration of the composition.

95. The method as claimed in claim 94, wherein plasma glucose concentration is lowered in about 1 hr to 7 hrs post administration of the composition.

* * * * *

UNITED STATES PATENT AND TRADEMARK OFFICE
CERTIFICATE OF CORRECTION

PATENT NO. : 7,081,465 B2
APPLICATION NO. : 10/693098
DATED : July 25, 2006
INVENTOR(S) : Devdutt Chaturvedi et al.

It is certified that error appears in the above-identified patent and that said Letters Patent is hereby corrected as shown below:

On Title Page, Item (75) should read,
Inventors: Devdutt Chaturvedi, Lucknow (IN); Atul Kumar, Lucknow (IN); Reema Rastogi, Lucknow (IN); ~~Arivend~~ Arvind Srivastava, Lucknow (IN); Priti Tewari, Lucknow (IN); Rehan Ahmad, Lucknow (IN); ~~Ramaesh~~ Ramesh Chander, Lucknow (IN); Anju Puri, Lucknow (IN); Geetika Bhatia, Lucknow (IN); ~~Farhar Rivizvi~~ Farhan Rizvi, Lucknow (IN); Anil Kumar Rastogi, Lucknow (IN); Suprabhat Ray, Lucknow (IN)

Signed and Sealed this

Twenty-eighth Day of November, 2006

JON W. DUDAS
*Director of the United States Patent and Trademark Office*